(12) United States Patent
Hoss et al.

(10) Patent No.: US 10,827,954 B2
(45) Date of Patent: Nov. 10, 2020

(54) CONTINUOUS ANALYTE MEASUREMENT SYSTEMS AND SYSTEMS AND METHODS FOR IMPLANTING THEM

(71) Applicant: Abbott Diabetes Care Inc., Alameda, CA (US)

(72) Inventors: Udo Hoss, Castro Valley, CA (US); John Charles Mazza, Long Beach, CA (US); Phu Le, Dublin, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 532 days.

(21) Appl. No.: 15/789,942

(22) Filed: Oct. 20, 2017

(65) Prior Publication Data

US 2018/0035931 A1 Feb. 8, 2018

Related U.S. Application Data

(63) Continuation of application No. 12/842,013, filed on Jul. 22, 2010, now Pat. No. 9,795,326.

(60) Provisional application No. 61/227,967, filed on Jul. 23, 2009.

(51) Int. Cl.
*A61B 5/00* (2006.01)
*A61B 5/145* (2006.01)
*A61B 5/1486* (2006.01)

(52) U.S. Cl.
CPC ...... *A61B 5/14532* (2013.01); *A61B 5/14865* (2013.01); *A61B 5/002* (2013.01); *A61B 2562/227* (2013.01)

(58) Field of Classification Search
CPC ............ A61B 5/14532; A61B 5/14865; A61B 2562/227; A61B 5/002; A61B 5/1495
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 3,960,497 A | 6/1976 | Acord et al. |
| 4,033,330 A | 7/1977 | Willis et al. |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,345,603 A | 8/1982 | Schulman |
| 4,349,728 A | 9/1982 | Phillips et al. |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

European Patent Application No. 10746954.6, Examination Report dated Dec. 14, 2017.

(Continued)

*Primary Examiner* — Christian Jang
(74) *Attorney, Agent, or Firm* — Baker Botts L.L.P.

(57) ABSTRACT

Low profile continuous analyte measurement systems and systems and methods for implantation within the skin of a patient are provided.

20 Claims, 14 Drawing Sheets

(56) References Cited

U.S. PATENT DOCUMENTS

| | | |
|---|---|---|
| 4,425,920 A | 1/1984 | Bourland et al. |
| 4,441,968 A | 4/1984 | Emmer et al. |
| 4,464,170 A | 8/1984 | Clemens et al. |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,847,785 A | 7/1989 | Stephens |
| 4,854,322 A | 8/1989 | Ash et al. |
| 4,890,620 A | 1/1990 | Gough |
| 4,925,268 A | 5/1990 | Iyer et al. |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,051,688 A | 9/1991 | Murase et al. |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,122,925 A | 6/1992 | Inpyn |
| 5,135,004 A | 8/1992 | Adams et al. |
| 5,145,381 A | 9/1992 | Volz |
| 5,165,407 A | 11/1992 | Wilson et al. |
| 5,202,261 A | 4/1993 | Musho et al. |
| 5,204,264 A | 4/1993 | Kaminer et al. |
| 5,210,778 A | 5/1993 | Massart |
| 5,228,449 A | 7/1993 | Christ et al. |
| 5,231,988 A | 8/1993 | Wernicke et al. |
| 5,246,867 A | 9/1993 | Lakowicz et al. |
| 5,251,126 A | 10/1993 | Kahn et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,715 A | 6/1994 | Berg |
| 5,320,725 A | 6/1994 | Gregg et al. |
| 5,322,063 A | 6/1994 | Allen et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,372,427 A | 12/1994 | Padovani et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,408,999 A | 4/1995 | Singh et al. |
| 5,410,326 A | 4/1995 | Goldstein |
| 5,411,647 A | 5/1995 | Johnson et al. |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,543,326 A | 8/1996 | Heller et al. |
| 5,552,997 A | 9/1996 | Massart |
| 5,555,190 A | 9/1996 | Derby et al. |
| 5,564,434 A | 10/1996 | Halperin et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,324 A | 5/1997 | Sarbach |
| 5,628,890 A | 5/1997 | Carter et al. |
| 5,653,239 A | 8/1997 | Pompei et al. |
| 5,660,163 A | 8/1997 | Schulman et al. |
| 5,665,222 A | 9/1997 | Heller et al. |
| 5,711,001 A | 1/1998 | Bussan et al. |
| 5,711,861 A | 1/1998 | Ward et al. |
| 5,726,646 A | 3/1998 | Bane et al. |
| 5,735,285 A | 4/1998 | Albert et al. |
| 5,748,103 A | 5/1998 | Flach et al. |
| 5,772,586 A | 6/1998 | Heinonen et al. |
| 5,791,344 A | 8/1998 | Schulman et al. |
| 5,797,940 A | 8/1998 | Mawhirt et al. |
| 5,814,020 A | 9/1998 | Gross |
| 5,820,551 A | 10/1998 | Hill et al. |
| 5,822,715 A | 10/1998 | Worthington et al. |
| 5,833,603 A | 11/1998 | Kovacs et al. |
| 5,842,189 A | 11/1998 | Keeler et al. |
| 5,858,001 A | 1/1999 | Tsals et al. |
| 5,899,855 A | 5/1999 | Brown |
| 5,914,026 A | 6/1999 | Blubaugh, Jr. et al. |
| 5,918,603 A | 7/1999 | Brown |
| 5,919,141 A | 7/1999 | Money et al. |
| 5,925,021 A | 7/1999 | Castellano et al. |
| 5,931,814 A | 8/1999 | Gross et al. |
| 5,942,979 A | 8/1999 | Luppino |
| 5,951,521 A | 9/1999 | Mastrototaro et al. |
| 5,954,643 A | 9/1999 | Van Antwerp et al. |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,980,708 A | 11/1999 | Champagne et al. |
| 5,993,411 A | 11/1999 | Choi |
| 5,995,860 A | 11/1999 | Sun et al. |
| 5,997,501 A | 12/1999 | Gross et al. |
| 6,001,067 A | 12/1999 | Shults et al. |
| 6,004,278 A | 12/1999 | Botich et al. |
| 6,024,699 A | 2/2000 | Surwit et al. |
| 6,028,413 A | 2/2000 | Brockmann |
| 6,049,727 A | 4/2000 | Crothall |
| 6,052,565 A | 4/2000 | Ishikura et al. |
| 6,066,243 A | 5/2000 | Anderson et al. |
| 6,071,391 A | 6/2000 | Gotoh et al. |
| 6,083,710 A | 7/2000 | Heller et al. |
| 6,088,608 A | 7/2000 | Schulman et al. |
| 6,091,976 A | 7/2000 | Pfeiffer et al. |
| 6,093,172 A | 7/2000 | Funderburk et al. |
| 6,096,364 A | 8/2000 | Bok et al. |
| 6,103,033 A | 8/2000 | Say et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,143,164 A | 11/2000 | Heller et al. |

(56) References Cited

U.S. PATENT DOCUMENTS

| | | |
|---|---|---|
| 6,144,837 A | 11/2000 | Quy |
| 6,157,850 A | 12/2000 | Diab et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,186,982 B1 | 2/2001 | Gross et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,223,283 B1 | 4/2001 | Chaiken et al. |
| 6,248,067 B1 | 6/2001 | Causey, III et al. |
| 6,254,586 B1 | 7/2001 | Mann et al. |
| 6,259,937 B1 | 7/2001 | Schulman et al. |
| 6,270,455 B1 | 8/2001 | Brown |
| 6,275,717 B1 | 8/2001 | Gross et al. |
| 6,283,761 B1 | 9/2001 | Joao |
| 6,284,478 B1 | 9/2001 | Heller et al. |
| 6,293,925 B1 | 9/2001 | Safabash et al. |
| 6,295,506 B1 | 9/2001 | Heinonen et al. |
| 6,299,347 B1 | 10/2001 | Pompei |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,314,317 B1 | 11/2001 | Willis |
| 6,322,801 B1 | 11/2001 | Lorenzi et al. |
| 6,329,161 B1 | 12/2001 | Heller et al. |
| 6,331,244 B1 | 12/2001 | Lewis et al. |
| 6,338,790 B1 | 1/2002 | Feldman et al. |
| 6,348,640 B1 | 2/2002 | Navot et al. |
| 6,359,270 B1 | 3/2002 | Bridson |
| 6,359,444 B1 | 3/2002 | Grimes |
| 6,360,888 B1 | 3/2002 | McIvor et al. |
| 6,366,794 B1 | 4/2002 | Moussy et al. |
| 6,368,141 B1 | 4/2002 | Van Antwerp et al. |
| 6,377,828 B1 | 4/2002 | Chaiken et al. |
| 6,377,894 B1 | 4/2002 | Deweese et al. |
| 6,379,301 B1 | 4/2002 | Worthington et al. |
| 6,418,332 B1 | 7/2002 | Mastrototaro et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,445,374 B2 | 9/2002 | Albert et al. |
| 6,461,496 B1 | 10/2002 | Feldman et al. |
| 6,471,689 B1 | 10/2002 | Joseph et al. |
| 6,478,736 B1 | 11/2002 | Mault |
| 6,482,176 B1 | 11/2002 | Wich |
| 6,484,046 B1 | 11/2002 | Say et al. |
| 6,493,069 B1 | 12/2002 | Nagashimada et al. |
| 6,497,655 B1 | 12/2002 | Linberg et al. |
| 6,498,043 B1 | 12/2002 | Schulman et al. |
| 6,503,381 B1 | 1/2003 | Gotoh et al. |
| 6,512,939 B1 | 1/2003 | Colvin et al. |
| 6,514,460 B1 | 2/2003 | Fendrock |
| 6,514,689 B2 | 2/2003 | Han et al. |
| 6,514,718 B2 | 2/2003 | Heller et al. |
| 6,522,927 B1 | 2/2003 | Bishay et al. |
| 6,540,891 B1 | 4/2003 | Stewart et al. |
| 6,546,268 B1 | 4/2003 | Ishikawa et al. |
| 6,549,796 B2 | 4/2003 | Sohrab |
| 6,551,494 B1 | 4/2003 | Heller et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,545 B2 | 6/2003 | Knobbe et al. |
| 6,574,490 B2 | 6/2003 | Abbink et al. |
| 6,576,101 B1 | 6/2003 | Heller et al. |
| 6,576,117 B1 | 6/2003 | Iketaki et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,631,281 B1 | 10/2003 | Kastle |
| 6,633,772 B2 | 10/2003 | Ford et al. |
| 6,635,014 B2 | 10/2003 | Starkweather et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulsen et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,721,582 B2 | 4/2004 | Trepagnier et al. |
| 6,730,025 B1 | 5/2004 | Platt |
| 6,730,200 B1 | 5/2004 | Stewart et al. |
| 6,733,446 B2 | 5/2004 | Lebel et al. |
| 6,736,957 B1 | 5/2004 | Forrow et al. |
| 6,740,075 B2 | 5/2004 | Lebel et al. |
| 6,740,518 B1 | 5/2004 | Duong et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,805,780 B1 | 10/2004 | Ryu et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,837,988 B2 | 1/2005 | Leong et al. |
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,954,662 B2 | 10/2005 | Freger et al. |
| 6,958,705 B2 | 10/2005 | Lebel et al. |
| 6,968,294 B2 | 11/2005 | Gutta et al. |
| 6,971,274 B2 | 12/2005 | Olin |
| 6,971,999 B2 | 12/2005 | Py et al. |
| 6,974,437 B2 | 12/2005 | Lebel et al. |
| 6,983,176 B2 | 1/2006 | Gardner et al. |
| 6,990,366 B2 | 1/2006 | Say et al. |

(56) References Cited

U.S. PATENT DOCUMENTS

| | | |
|---|---|---|
| 6,997,907 B2 | 2/2006 | Safabash et al. |
| 6,998,247 B2 | 2/2006 | Monfre et al. |
| 6,999,854 B2 | 2/2006 | Roth |
| 7,003,336 B2 | 2/2006 | Holker et al. |
| 7,003,340 B2 | 2/2006 | Say et al. |
| 7,003,341 B2 | 2/2006 | Say et al. |
| 7,011,630 B2 | 3/2006 | Desai et al. |
| 7,015,817 B2 | 3/2006 | Copley et al. |
| 7,016,713 B2 | 3/2006 | Gardner et al. |
| 7,022,072 B2 | 4/2006 | Fox et al. |
| 7,022,219 B2 | 4/2006 | Mansouri et al. |
| 7,024,245 B2 | 4/2006 | Lebel et al. |
| 7,025,425 B2 | 4/2006 | Kovatchev et al. |
| 7,027,848 B2 | 4/2006 | Robinson et al. |
| 7,027,931 B1 | 4/2006 | Jones et al. |
| 7,041,068 B2 | 5/2006 | Freeman et al. |
| 7,041,468 B2 | 5/2006 | Drucker et al. |
| 7,046,153 B2 | 5/2006 | Oja et al. |
| 7,052,472 B1 | 5/2006 | Miller et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,073,246 B2 | 7/2006 | Bhullar et al. |
| 7,074,307 B2 | 7/2006 | Simpson et al. |
| 7,081,195 B2 | 7/2006 | Simpson et al. |
| 7,092,891 B2 | 8/2006 | Maus et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,153,265 B2 | 12/2006 | Vachon |
| 7,155,290 B2 | 12/2006 | Von Arx et al. |
| 7,167,818 B2 | 1/2007 | Brown |
| 7,171,274 B2 | 1/2007 | Starkweather et al. |
| 7,174,199 B2 | 2/2007 | Berner et al. |
| 7,179,226 B2 | 2/2007 | Crothall et al. |
| 7,183,102 B2 | 2/2007 | Monfre et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,207,974 B2 | 4/2007 | Safabash et al. |
| 7,225,535 B2 | 6/2007 | Feldman et al. |
| 7,226,442 B2 | 6/2007 | Sheppard et al. |
| 7,226,978 B2 | 6/2007 | Tapsak et al. |
| 7,258,673 B2 | 8/2007 | Racchini et al. |
| 7,267,665 B2 | 9/2007 | Steil et al. |
| 7,276,029 B2 | 10/2007 | Goode, Jr. et al. |
| 7,278,983 B2 | 10/2007 | Ireland et al. |
| 7,286,894 B1 | 10/2007 | Grant et al. |
| 7,291,497 B2 | 11/2007 | Holmes et al. |
| 7,295,867 B2 | 11/2007 | Berner et al. |
| 7,299,082 B2 | 11/2007 | Feldman et al. |
| 7,310,544 B2 | 12/2007 | Brister et al. |
| 7,317,938 B2 | 1/2008 | Lorenz et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,384,397 B2 | 6/2008 | Zhang et al. |
| 7,386,937 B2 | 6/2008 | Bhullar et al. |
| 7,404,796 B2 | 7/2008 | Ginsberg |
| 7,424,318 B2 | 9/2008 | Brister et al. |
| 7,433,727 B2 | 10/2008 | Ward et al. |
| 7,460,898 B2 | 12/2008 | Brister et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,565,197 B2 | 7/2009 | Haubrich et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,613,491 B2 | 11/2009 | Boock et al. |
| 7,615,007 B2 | 11/2009 | Shults et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,651,845 B2 | 1/2010 | Doyle, III et al. |
| 7,653,425 B2 | 1/2010 | Hayter et al. |
| 7,654,956 B2 | 2/2010 | Brister et al. |
| 7,657,297 B2 | 2/2010 | Simpson et al. |
| 7,659,823 B1 | 2/2010 | Killian et al. |
| 7,699,775 B2 | 4/2010 | Desai et al. |
| 7,699,964 B2 | 4/2010 | Feldman et al. |
| 7,711,402 B2 | 5/2010 | Shults et al. |
| 7,711,493 B2 | 5/2010 | Bartkowiak et al. |
| 7,713,574 B2 | 5/2010 | Brister et al. |
| 7,715,893 B2 | 5/2010 | Kamath et al. |
| 7,729,737 B2 | 6/2010 | Ward |
| 7,736,310 B2 | 6/2010 | Taub et al. |
| 7,741,734 B2 | 6/2010 | Joannopoulos et al. |
| 7,751,864 B2 | 7/2010 | Buck, Jr. |
| 7,766,829 B2 | 8/2010 | Sloan et al. |
| 7,768,386 B2 | 8/2010 | Hayter et al. |
| 7,768,387 B2 | 8/2010 | Fennell et al. |
| 7,774,145 B2 | 8/2010 | Bruaker et al. |
| 7,775,444 B2 | 8/2010 | DeRocco et al. |
| 7,778,680 B2 | 8/2010 | Goode, Jr. et al. |
| 7,778,795 B2 | 8/2010 | Fukushima et al. |
| 7,779,332 B2 | 8/2010 | Karr et al. |
| 7,811,231 B2 | 10/2010 | Jin et al. |
| 7,813,809 B2 | 10/2010 | Strother et al. |
| 7,826,382 B2 | 11/2010 | Sicurello et al. |
| 7,826,981 B2 | 11/2010 | Goode, Jr. et al. |
| 7,857,760 B2 | 12/2010 | Brister et al. |
| 7,866,026 B1 | 1/2011 | Wang et al. |
| 7,882,611 B2 | 2/2011 | Shah et al. |
| 7,885,697 B2 | 2/2011 | Brister et al. |
| 7,889,069 B2 | 2/2011 | Fifolt et al. |
| 7,899,545 B2 | 3/2011 | John |
| 7,905,833 B2 | 3/2011 | Brister et al. |
| 7,911,010 B2 | 3/2011 | Stetter |
| 7,914,450 B2 | 3/2011 | Goode, Jr. et al. |
| 7,920,906 B2 | 4/2011 | Goode et al. |
| 7,920,907 B2 | 4/2011 | McGarraugh et al. |
| 7,928,850 B2 | 4/2011 | Hayter et al. |
| 7,938,797 B2 | 5/2011 | Estes |
| 7,941,200 B2 | 5/2011 | Weinert et al. |
| 7,946,984 B2 | 5/2011 | Brister et al. |
| 7,946,985 B2 | 5/2011 | Mastrototaro et al. |
| 7,954,385 B2 | 6/2011 | Raisanen |
| 7,970,449 B2 | 6/2011 | Ward |
| 7,972,296 B2 | 7/2011 | Braig et al. |
| 7,974,672 B2 | 7/2011 | Shults et al. |
| 7,976,466 B2 | 7/2011 | Ward et al. |
| 7,978,063 B2 | 7/2011 | Baldus et al. |
| 7,996,158 B2 | 8/2011 | Hayter et al. |
| 8,005,524 B2 | 8/2011 | Brauker et al. |
| 8,010,174 B2 | 8/2011 | Goode et al. |
| 8,010,256 B2 | 8/2011 | Oowada |
| 8,060,173 B2 | 11/2011 | Goode, Jr. et al. |
| 8,103,471 B2 | 1/2012 | Hayter |
| 8,140,312 B2 | 3/2012 | Hayter et al. |
| 8,150,321 B2 | 4/2012 | Winter et al. |
| 8,150,516 B2 | 4/2012 | Levine et al. |
| 8,160,670 B2 | 4/2012 | Quyang et al. |

(56) References Cited

U.S. PATENT DOCUMENTS

| | | |
|---|---|---|
| 8,170,803 B2 | 5/2012 | Kamath et al. |
| 8,179,266 B2 | 5/2012 | Hermle |
| 8,192,394 B2 | 6/2012 | Estes et al. |
| 8,216,138 B1 | 7/2012 | McGarraugh et al. |
| 8,239,166 B2 | 8/2012 | Hayter et al. |
| 8,255,026 B1 | 8/2012 | Al-Ali |
| 8,260,558 B2 | 9/2012 | Hayter et al. |
| 8,282,549 B2 | 10/2012 | Brauker et al. |
| 8,346,335 B2 | 1/2013 | Harper et al. |
| 8,346,337 B2 | 1/2013 | Heller et al. |
| 8,374,668 B1 | 2/2013 | Hayter et al. |
| 8,376,945 B2 | 2/2013 | Hayter et al. |
| 8,377,271 B2 | 2/2013 | Mao et al. |
| 8,409,093 B2 | 4/2013 | Bugler |
| 8,444,560 B2 | 5/2013 | Hayter et al. |
| 8,461,985 B2 | 6/2013 | Fennell et al. |
| 8,465,425 B2 | 6/2013 | Heller et al. |
| 8,484,005 B2 | 7/2013 | Hayter et al. |
| 8,543,354 B2 | 9/2013 | Luo et al. |
| 8,560,038 B2 | 10/2013 | Hayter et al. |
| 8,571,808 B2 | 10/2013 | Hayter |
| 8,583,205 B2 | 11/2013 | Budiman et al. |
| 8,597,570 B2 | 12/2013 | Terashima et al. |
| 8,600,681 B2 | 12/2013 | Hayter et al. |
| 8,612,163 B2 | 12/2013 | Hayter et al. |
| 8,657,746 B2 | 2/2014 | Roy |
| 8,682,615 B2 | 3/2014 | Hayter et al. |
| 8,688,188 B2 | 4/2014 | Heller et al. |
| 8,710,993 B2 | 4/2014 | Hayter et al. |
| 8,834,366 B2 | 9/2014 | Hayter et al. |
| 8,845,536 B2 | 9/2014 | Brauker et al. |
| 9,060,719 B2 | 6/2015 | Hayter et al. |
| 9,289,179 B2 | 3/2016 | Hayter et al. |
| 9,398,872 B2 | 7/2016 | Hayter et al. |
| 9,408,566 B2 | 8/2016 | Hayter et al. |
| 9,439,586 B2 | 9/2016 | Bugler |
| 9,483,608 B2 | 11/2016 | Hayter et al. |
| 9,558,325 B2 | 1/2017 | Hayter et al. |
| 9,743,872 B2 | 8/2017 | Hayter et al. |
| 2001/0031931 A1 | 10/2001 | Cunningham et al. |
| 2001/0037366 A1 | 11/2001 | Webb et al. |
| 2002/0016534 A1 | 2/2002 | Trepagnier et al. |
| 2002/0019022 A1 | 2/2002 | Dunn et al. |
| 2002/0032374 A1 | 3/2002 | Holker et al. |
| 2002/0042090 A1 | 4/2002 | Heller et al. |
| 2002/0050250 A1 | 5/2002 | Peterson et al. |
| 2002/0052618 A1 | 5/2002 | Haar et al. |
| 2002/0054320 A1 | 5/2002 | Ogino |
| 2002/0055711 A1 | 5/2002 | Lavi et al. |
| 2002/0065454 A1 | 5/2002 | Lebel et al. |
| 2002/0068860 A1 | 6/2002 | Clark |
| 2002/0095076 A1 | 7/2002 | Krausman et al. |
| 2002/0103499 A1 | 8/2002 | Perez et al. |
| 2002/0106709 A1 | 8/2002 | Potts et al. |
| 2002/0117639 A1 | 8/2002 | Paolini et al. |
| 2002/0120186 A1 | 8/2002 | Keimel |
| 2002/0128594 A1 | 9/2002 | Das et al. |
| 2002/0147135 A1 | 10/2002 | Schnell |
| 2002/0150959 A1 | 10/2002 | Lejeunne et al. |
| 2002/0161288 A1 | 10/2002 | Shin et al. |
| 2003/0023317 A1 | 1/2003 | Brauker et al. |
| 2003/0023461 A1 | 1/2003 | Quintanilla et al. |
| 2003/0028089 A1 | 2/2003 | Galley et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0050546 A1 | 3/2003 | Desai et al. |
| 2003/0054428 A1 | 3/2003 | Monfre et al. |
| 2003/0060692 A1 | 3/2003 | Ruchti et al. |
| 2003/0060753 A1 | 3/2003 | Starkweather et al. |
| 2003/0065308 A1 | 4/2003 | Lebel et al. |
| 2003/0100040 A1 | 5/2003 | Bonnecaze et al. |
| 2003/0100821 A1 | 5/2003 | Heller et al. |
| 2003/0114897 A1 | 6/2003 | Von Arx et al. |
| 2003/0130616 A1 | 7/2003 | Steil et al. |
| 2003/0134347 A1 | 7/2003 | Heller et al. |
| 2003/0147515 A1 | 8/2003 | Kai et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0191377 A1 | 10/2003 | Robinson et al. |
| 2003/0199744 A1 | 10/2003 | Buse et al. |
| 2003/0199790 A1 | 10/2003 | Boecker et al. |
| 2003/0212379 A1 | 11/2003 | Bylund et al. |
| 2003/0217966 A1 | 11/2003 | Tapsak et al. |
| 2003/0223906 A1 | 12/2003 | McAllister et al. |
| 2003/0235817 A1 | 12/2003 | Bartkowiak et al. |
| 2004/0010186 A1 | 1/2004 | Kimball et al. |
| 2004/0010207 A1 | 1/2004 | Flaherty et al. |
| 2004/0011671 A1 | 1/2004 | Shults et al. |
| 2004/0024553 A1 | 2/2004 | Monfre et al. |
| 2004/0034289 A1 | 2/2004 | Teller et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0063435 A1 | 4/2004 | Sakamoto et al. |
| 2004/0064068 A1 | 4/2004 | DeNuzzio et al. |
| 2004/0099529 A1 | 5/2004 | Mao et al. |
| 2004/0106858 A1 | 6/2004 | Say et al. |
| 2004/0111017 A1 | 6/2004 | Say et al. |
| 2004/0116847 A1 | 6/2004 | Wall |
| 2004/0116866 A1 | 6/2004 | Gorman et al. |
| 2004/0117204 A1 | 6/2004 | Mazar et al. |
| 2004/0122353 A1 | 6/2004 | Shahmirian et al. |
| 2004/0133164 A1 | 7/2004 | Funderburk et al. |
| 2004/0133390 A1 | 7/2004 | Osorio et al. |
| 2004/0135571 A1 | 7/2004 | Uutela et al. |
| 2004/0135684 A1 | 7/2004 | Steinthal et al. |
| 2004/0138588 A1 | 7/2004 | Saikley et al. |
| 2004/0142403 A1 | 7/2004 | Hetzel et al. |
| 2004/0147872 A1 | 7/2004 | Thompson |
| 2004/0147996 A1 | 7/2004 | Miazga et al. |
| 2004/0152622 A1 | 8/2004 | Keith et al. |
| 2004/0162678 A1 | 8/2004 | Hetzel et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193020 A1 | 9/2004 | Chiba et al. |
| 2004/0193090 A1 | 9/2004 | Lebel et al. |
| 2004/0199056 A1 | 10/2004 | Husemann et al. |
| 2004/0199059 A1 | 10/2004 | Brauker et al. |
| 2004/0204687 A1 | 10/2004 | Mogensen et al. |
| 2004/0204868 A1 | 10/2004 | Maynard et al. |
| 2004/0219664 A1 | 11/2004 | Heller et al. |
| 2004/0223985 A1 | 11/2004 | Dunfiled et al. |
| 2004/0225338 A1 | 11/2004 | Lebel et al. |
| 2004/0236200 A1 | 11/2004 | Say et al. |
| 2004/0249253 A1 | 12/2004 | Racchini et al. |
| 2004/0249254 A1 | 12/2004 | Racchini et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0001024 A1 | 1/2005 | Kusaka et al. |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0017864 A1 | 1/2005 | Tsoukalis |
| 2005/0021066 A1 | 1/2005 | Kuhr et al. |
| 2005/0027177 A1 | 2/2005 | Shin et al. |
| 2005/0027180 A1 | 2/2005 | Goode et al. |
| 2005/0027181 A1 | 2/2005 | Goode et al. |
| 2005/0027182 A1 | 2/2005 | Siddiqui et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0043598 A1 | 2/2005 | Goode, Jr. et al. |
| 2005/0049179 A1 | 3/2005 | Davidson et al. |
| 2005/0049473 A1 | 3/2005 | Desai et al. |
| 2005/0070774 A1 | 3/2005 | Addison et al. |
| 2005/0070777 A1 | 3/2005 | Cho et al. |

(56) References Cited

U.S. PATENT DOCUMENTS

| | | |
|---|---|---|
| 2005/0090607 A1 | 4/2005 | Tapsak et al. |
| 2005/0096516 A1 | 5/2005 | Soykan et al. |
| 2005/0096520 A1 | 5/2005 | Maekawa et al. |
| 2005/0103624 A1 | 5/2005 | Bhullar et al. |
| 2005/0112169 A1 | 5/2005 | Brauker et al. |
| 2005/0113648 A1 | 5/2005 | Yang et al. |
| 2005/0113886 A1 | 5/2005 | Fischell et al. |
| 2005/0114068 A1 | 5/2005 | Chey et al. |
| 2005/0115832 A1 | 6/2005 | Simpson et al. |
| 2005/0116683 A1 | 6/2005 | Cheng et al. |
| 2005/0121322 A1 | 6/2005 | Say et al. |
| 2005/0131346 A1 | 6/2005 | Douglas |
| 2005/0134731 A1 | 6/2005 | Lee et al. |
| 2005/0137530 A1 | 6/2005 | Campbell et al. |
| 2005/0143635 A1 | 6/2005 | Kamath et al. |
| 2005/0154271 A1 | 7/2005 | Rasdal et al. |
| 2005/0173245 A1 | 8/2005 | Feldman et al. |
| 2005/0176136 A1 | 8/2005 | Burd et al. |
| 2005/0182306 A1 | 8/2005 | Sloan |
| 2005/0187442 A1 | 8/2005 | Cho et al. |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0196821 A1 | 9/2005 | Monfre et al. |
| 2005/0197793 A1 | 9/2005 | Baker, Jr. |
| 2005/0199494 A1 | 9/2005 | Say et al. |
| 2005/0203360 A1 | 9/2005 | Brauker et al. |
| 2005/0204134 A1 | 9/2005 | Von Arx et al. |
| 2005/0211572 A1 | 9/2005 | Buck et al. |
| 2005/0214892 A1 | 9/2005 | Kovatchev et al. |
| 2005/0215871 A1 | 9/2005 | Feldman et al. |
| 2005/0236361 A1 | 10/2005 | Ufer et al. |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0251033 A1 | 11/2005 | Scarantino et al. |
| 2005/0269214 A1 | 12/2005 | Lee |
| 2005/0272985 A1 | 12/2005 | Kotulla et al. |
| 2005/0277164 A1 | 12/2005 | Drucker et al. |
| 2005/0277912 A1 | 12/2005 | John |
| 2005/0287620 A1 | 12/2005 | Heller et al. |
| 2006/0001538 A1 | 1/2006 | Kraft et al. |
| 2006/0001551 A1 | 1/2006 | Kraft et al. |
| 2006/0009727 A1 | 1/2006 | O'Mahony et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0017923 A1 | 1/2006 | Ruchti et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0020300 A1 | 1/2006 | Nghiem et al. |
| 2006/0025662 A1 | 2/2006 | Buse et al. |
| 2006/0025663 A1 | 2/2006 | Talbot et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0058588 A1 | 3/2006 | Zdeblick |
| 2006/0079740 A1 | 4/2006 | Silver et al. |
| 2006/0091006 A1 | 5/2006 | Wang et al. |
| 2006/0142651 A1 | 6/2006 | Brister et al. |
| 2006/0156796 A1 | 7/2006 | Burke et al. |
| 2006/0166629 A1 | 7/2006 | Reggiardo |
| 2006/0169599 A1 | 8/2006 | Feldman et al. |
| 2006/0173444 A1 | 8/2006 | Choy et al. |
| 2006/0183984 A1 | 8/2006 | Dobbles et al. |
| 2006/0189851 A1 | 8/2006 | Tvig et al. |
| 2006/0189863 A1 | 8/2006 | Peyser et al. |
| 2006/0193375 A1 | 8/2006 | Lee |
| 2006/0202805 A1 | 9/2006 | Schulman et al. |
| 2006/0211072 A1 | 9/2006 | Ryan et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0229512 A1 | 10/2006 | Petisce et al. |
| 2006/0233839 A1 | 10/2006 | Jacquet |
| 2006/0247508 A1 | 11/2006 | Fennell |
| 2006/0247710 A1 | 11/2006 | Goetz et al. |
| 2006/0247985 A1 | 11/2006 | Liamos et al. |
| 2006/0253085 A1 | 11/2006 | Geismar et al. |
| 2006/0253086 A1 | 11/2006 | Moberg et al. |
| 2006/0253296 A1 | 11/2006 | Liisberg et al. |
| 2006/0258929 A1 | 11/2006 | Goode et al. |
| 2006/0281985 A1 | 12/2006 | Ward et al. |
| 2006/0287591 A1 | 12/2006 | Ocvirk et al. |
| 2006/0287691 A1 | 12/2006 | Drew |
| 2006/0290496 A1 | 12/2006 | Peeters et al. |
| 2006/0293576 A1 | 12/2006 | Van Antwerp et al. |
| 2006/0293607 A1 | 12/2006 | Alt et al. |
| 2007/0007133 A1 | 1/2007 | Mang et al. |
| 2007/0010950 A1 | 1/2007 | Abensour et al. |
| 2007/0017983 A1 | 1/2007 | Frank et al. |
| 2007/0027381 A1 | 2/2007 | Stafford |
| 2007/0027507 A1 | 2/2007 | Burdett et al. |
| 2007/0032706 A1 | 2/2007 | Kamath et al. |
| 2007/0032717 A1 | 2/2007 | Brister et al. |
| 2007/0038044 A1 | 2/2007 | Dobbles et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0060869 A1 | 3/2007 | Tolle et al. |
| 2007/0060979 A1 | 3/2007 | Strother et al. |
| 2007/0066873 A1 | 3/2007 | Kamath et al. |
| 2007/0066956 A1 | 3/2007 | Finkel |
| 2007/0068807 A1 | 3/2007 | Feldman et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0093786 A1 | 4/2007 | Goldsmith et al. |
| 2007/0094216 A1 | 4/2007 | Mathias et al. |
| 2007/0095661 A1 | 5/2007 | Wang et al. |
| 2007/0106135 A1 | 5/2007 | Sloan et al. |
| 2007/0108048 A1 | 5/2007 | Wang et al. |
| 2007/0118030 A1 | 5/2007 | Bruce et al. |
| 2007/0118405 A1 | 5/2007 | Campbell et al. |
| 2007/0129621 A1 | 6/2007 | Kellogg et al. |
| 2007/0135696 A1 | 6/2007 | Ward |
| 2007/0135698 A1 | 6/2007 | Shah et al. |
| 2007/0149875 A1 | 6/2007 | Ouyang et al. |
| 2007/0153705 A1 | 7/2007 | Rosar et al. |
| 2007/0156033 A1 | 7/2007 | Causey, III et al. |
| 2007/0156094 A1 | 7/2007 | Safabash et al. |
| 2007/0161880 A1 | 7/2007 | Say et al. |
| 2007/0163880 A1 | 7/2007 | Woo et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173711 A1 | 7/2007 | Shah et al. |
| 2007/0191701 A1 | 8/2007 | Feldman et al. |
| 2007/0191702 A1 | 8/2007 | Yodfat et al. |
| 2007/0199818 A1 | 8/2007 | Petyt et al. |
| 2007/0202562 A1 | 8/2007 | Curry et al. |
| 2007/0203407 A1 | 8/2007 | Hoss et al. |
| 2007/0203966 A1 | 8/2007 | Brauker et al. |
| 2007/0208244 A1 | 9/2007 | Brauker et al. |
| 2007/0208246 A1 | 9/2007 | Brauker et al. |
| 2007/0213657 A1 | 9/2007 | Jennewine et al. |
| 2007/0219496 A1 | 9/2007 | Kamen et al. |
| 2007/0227911 A1 | 10/2007 | Wang et al. |
| 2007/0228071 A1 | 10/2007 | Kamen et al. |
| 2007/0232878 A1 | 10/2007 | Kovatchev et al. |

(56) References Cited

U.S. PATENT DOCUMENTS

| | | |
|---|---|---|
| 2007/0233013 A1 | 10/2007 | Schoenberg et al. |
| 2007/0235331 A1 | 10/2007 | Simpson et al. |
| 2007/0244379 A1 | 10/2007 | Boock et al. |
| 2007/0244383 A1 | 10/2007 | Talbot et al. |
| 2007/0249922 A1 | 10/2007 | Peyser et al. |
| 2007/0255321 A1 | 11/2007 | Gelber et al. |
| 2007/0255348 A1 | 11/2007 | Holtzclaw |
| 2007/0255531 A1 | 11/2007 | Drew |
| 2007/0258395 A1 | 11/2007 | Jollota et al. |
| 2007/0271285 A1 | 11/2007 | Eichorn et al. |
| 2007/0299617 A1 | 12/2007 | Willis |
| 2008/0004515 A1 | 1/2008 | Jennewine et al. |
| 2008/0004601 A1 | 1/2008 | Jennewine et al. |
| 2008/0009692 A1 | 1/2008 | Stafford |
| 2008/0012701 A1 | 1/2008 | Kass et al. |
| 2008/0017522 A1 | 1/2008 | Heller et al. |
| 2008/0019869 A1 | 1/2008 | Nakamura et al. |
| 2008/0021436 A1 | 1/2008 | Wolpert et al. |
| 2008/0021666 A1 | 1/2008 | Goode, Jr. et al. |
| 2008/0021972 A1 | 1/2008 | Huelskamp et al. |
| 2008/0029391 A1 | 2/2008 | Mao et al. |
| 2008/0030369 A1 | 2/2008 | Mann et al. |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0057484 A1 | 3/2008 | Miyata et al. |
| 2008/0058625 A1 | 3/2008 | McGarraugh et al. |
| 2008/0058626 A1 | 3/2008 | Miyata et al. |
| 2008/0058678 A1 | 3/2008 | Miyata et al. |
| 2008/0058773 A1 | 3/2008 | John |
| 2008/0060955 A1 | 3/2008 | Goodnow |
| 2008/0061961 A1 | 3/2008 | John |
| 2008/0064937 A1 | 3/2008 | McGarraugh et al. |
| 2008/0064943 A1 | 3/2008 | Talbot et al. |
| 2008/0066305 A1 | 3/2008 | Wang et al. |
| 2008/0071156 A1 | 3/2008 | Brister et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0077048 A1 | 3/2008 | Escutia et al. |
| 2008/0081977 A1 | 4/2008 | Hayter et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0092638 A1 | 4/2008 | Brenneman et al. |
| 2008/0102441 A1 | 5/2008 | Chen et al. |
| 2008/0108942 A1 | 5/2008 | Brister et al. |
| 2008/0114228 A1 | 5/2008 | McCluskey et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0148873 A1 | 6/2008 | Wang |
| 2008/0156662 A1 | 7/2008 | Wu et al. |
| 2008/0161664 A1 | 7/2008 | Mastrototaro et al. |
| 2008/0161666 A1 | 7/2008 | Feldman et al. |
| 2008/0172205 A1 | 7/2008 | Breton et al. |
| 2008/0177149 A1 | 7/2008 | Weinert et al. |
| 2008/0177165 A1 | 7/2008 | Blomquist et al. |
| 2008/0182537 A1 | 7/2008 | Manku et al. |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194934 A1 | 8/2008 | Ray et al. |
| 2008/0194935 A1 | 8/2008 | Brister et al. |
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195049 A1 | 8/2008 | Thalmann et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0201325 A1 | 8/2008 | Doniger et al. |
| 2008/0208025 A1 | 8/2008 | Shults et al. |
| 2008/0208026 A1 | 8/2008 | Noujaim et al. |
| 2008/0314395 A1 | 8/2008 | Kovatchev et al. |
| 2008/0214900 A1 | 9/2008 | Fennell et al. |
| 2008/0214910 A1 | 9/2008 | Buck |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234663 A1 | 9/2008 | Yodfat et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0254544 A1 | 10/2008 | Modzelewski et al. |
| 2008/0255438 A1 | 10/2008 | Saidara et al. |
| 2008/0262469 A1 | 10/2008 | Brister et al. |
| 2008/0267823 A1 | 10/2008 | Wang et al. |
| 2008/0269714 A1 | 10/2008 | Mastrototaro et al. |
| 2008/0269723 A1 | 10/2008 | Mastrototaro et al. |
| 2008/0275313 A1 | 11/2008 | Brister et al. |
| 2008/0281178 A1 | 11/2008 | Chaung et al. |
| 2008/0287761 A1 | 11/2008 | Hayter |
| 2008/0287762 A1 | 11/2008 | Hayter |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0294024 A1 | 11/2008 | Cosentino et al. |
| 2008/0296155 A1 | 12/2008 | Shults et al. |
| 2008/0300572 A1 | 12/2008 | Rankers et al. |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312844 A1 | 12/2008 | Hayter et al. |
| 2008/0319085 A1 | 12/2008 | Wright et al. |
| 2008/0319279 A1 | 12/2008 | Ramsay et al. |
| 2008/0319295 A1 | 12/2008 | Bernstein et al. |
| 2009/0005665 A1 | 1/2009 | Hayter et al. |
| 2009/0005666 A1 | 1/2009 | Shin et al. |
| 2009/0005729 A1 | 1/2009 | Hendrixson et al. |
| 2009/0006061 A1 | 1/2009 | Thukral et al. |
| 2009/0012376 A1 | 1/2009 | Agus |
| 2009/0012379 A1 | 1/2009 | Goode, Jr. et al. |
| 2009/0018424 A1 | 1/2009 | Kamath et al. |
| 2009/0018425 A1 | 1/2009 | Ouyang et al. |
| 2009/0020502 A1 | 1/2009 | Bhullar et al. |
| 2009/0030293 A1 | 1/2009 | Cooper et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0040022 A1 | 2/2009 | Finkenzeller |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048503 A1 | 2/2009 | Dalal et al. |
| 2009/0054745 A1 | 2/2009 | Jennewine et al. |
| 2009/0054747 A1 | 2/2009 | Fennell |
| 2009/0054748 A1 | 2/2009 | Feldman et al. |
| 2009/0054753 A1 | 2/2009 | Robinson et al. |
| 2009/0062633 A1 | 3/2009 | Brauker et al. |
| 2009/0062635 A1 | 3/2009 | Brauker et al. |
| 2009/0063187 A1 | 3/2009 | Johnson et al. |
| 2009/0069750 A1 | 3/2009 | Schraga |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0085768 A1 | 4/2009 | Patel et al. |
| 2009/0085873 A1 | 4/2009 | Betts et al. |
| 2009/0093687 A1 | 4/2009 | Telfort et al. |
| 2009/0093695 A1 | 4/2009 | Nakamura et al. |

(56) References Cited

U.S. PATENT DOCUMENTS

| | | |
|---|---|---|
| 2009/0099436 A1 | 4/2009 | Brister et al. |
| 2009/0102678 A1 | 4/2009 | Mazza et al. |
| 2009/0105568 A1 | 4/2009 | Bugler |
| 2009/0105570 A1 | 4/2009 | Sloan et al. |
| 2009/0105571 A1 | 4/2009 | Fennell et al. |
| 2009/0105636 A1 | 4/2009 | Hayter et al. |
| 2009/0112478 A1 | 4/2009 | Mueller, Jr. et al. |
| 2009/0112626 A1 | 4/2009 | Talbot et al. |
| 2009/0124877 A1 | 5/2009 | Goode, Jr. et al. |
| 2009/0124878 A1 | 5/2009 | Goode, Jr. et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1* | 5/2009 | Leach .................. A61B 5/6848 600/309 |
| 2009/0131776 A1 | 5/2009 | Simpson et al. |
| 2009/0131777 A1 | 5/2009 | Simpson et al. |
| 2009/0131860 A1 | 5/2009 | Nielsen |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0145775 A1 | 6/2009 | Chu et al. |
| 2009/0149728 A1 | 6/2009 | Van Antwerp et al. |
| 2009/0150186 A1 | 6/2009 | Cohen et al. |
| 2009/0156919 A1 | 6/2009 | Brister et al. |
| 2009/0156920 A1 | 6/2009 | Kotzan et al. |
| 2009/0156924 A1 | 6/2009 | Shariati et al. |
| 2009/0163789 A1* | 6/2009 | Say .......................... C12Q 1/54 600/345 |
| 2009/0163790 A1 | 6/2009 | Brister et al. |
| 2009/0163791 A1 | 6/2009 | Brister et al. |
| 2009/0163855 A1 | 6/2009 | Shin et al. |
| 2009/0177068 A1 | 7/2009 | Stivoric et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216100 A1 | 8/2009 | Ebner et al. |
| 2009/0216103 A1 | 8/2009 | Brister et al. |
| 2009/0227855 A1 | 9/2009 | Hill et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0240440 A1 | 9/2009 | Shurabura et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0247931 A1 | 10/2009 | Damgaard-Sorensen |
| 2009/0259118 A1 | 10/2009 | Feldman et al. |
| 2009/0275817 A1 | 11/2009 | Feldman et al. |
| 2009/0281406 A1 | 11/2009 | McGarraugh et al. |
| 2009/0287073 A1 | 11/2009 | Boock et al. |
| 2009/0287074 A1 | 11/2009 | Shults et al. |
| 2009/0292188 A1 | 11/2009 | Hoss et al. |
| 2009/0294277 A1 | 12/2009 | Thomas et al. |
| 2009/0296742 A1 | 12/2009 | Sicurello et al. |
| 2009/0298182 A1 | 12/2009 | Schulat et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010329 A1 | 1/2010 | Taub et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0022988 A1 | 1/2010 | Wochner et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0064764 A1 | 3/2010 | Hayter et al. |
| 2010/0076283 A1 | 3/2010 | Simpson et al. |
| 2010/0081908 A1 | 4/2010 | Dobbles et al. |
| 2010/0081909 A1 | 4/2010 | Budiman et al. |
| 2010/0081910 A1 | 4/2010 | Brister et al. |
| 2010/0081953 A1 | 4/2010 | Syeda-Mahmood et al. |
| 2010/0087724 A1 | 4/2010 | Brauker et al. |
| 2010/0094111 A1 | 4/2010 | Heller et al. |
| 2010/0094251 A1 | 4/2010 | Estes et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0105999 A1 | 4/2010 | Dixon et al. |
| 2010/0119693 A1 | 5/2010 | Tapsak et al. |
| 2010/0121167 A1 | 5/2010 | McGarraugh et al. |
| 2010/0121169 A1 | 5/2010 | Petisce et al. |
| 2010/0141656 A1 | 6/2010 | Krieftewirth |
| 2010/0152554 A1 | 6/2010 | Steine et al. |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0185175 A1 | 7/2010 | Kamen et al. |
| 2010/0191082 A1 | 7/2010 | Brister et al. |
| 2010/0191085 A1 | 7/2010 | Budiman |
| 2010/0191472 A1 | 7/2010 | Doniger et al. |
| 2010/0198034 A1 | 8/2010 | Thomas et al. |
| 2010/0198142 A1 | 8/2010 | Sloan et al. |
| 2010/0204557 A1 | 8/2010 | Kiaie et al. |
| 2010/0213057 A1 | 8/2010 | Feldman et al. |
| 2010/0213080 A1 | 8/2010 | Celentano et al. |
| 2010/0230285 A1 | 9/2010 | Hoss et al. |
| 2010/0234710 A1 | 9/2010 | Budiman et al. |
| 2010/0261987 A1 | 10/2010 | Kamath et al. |
| 2010/0274111 A1 | 10/2010 | Say et al. |
| 2010/0274515 A1 | 10/2010 | Hoss et al. |
| 2010/0280441 A1 | 11/2010 | Willinska et al. |
| 2010/0313105 A1 | 12/2010 | Nekoomaram et al. |
| 2010/0317952 A1 | 12/2010 | Budiman et al. |
| 2010/0324392 A1 | 12/2010 | Yee et al. |
| 2010/0326842 A1 | 12/2010 | Mazza et al. |
| 2011/0004085 A1 | 1/2011 | Mensinger et al. |
| 2011/0021889 A1 | 1/2011 | Hoss et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |
| 2011/0028815 A1 | 2/2011 | Simpson et al. |
| 2011/0028816 A1 | 2/2011 | Simpson et al. |
| 2011/0031986 A1 | 2/2011 | Bhat et al. |
| 2011/0040163 A1 | 2/2011 | Telson et al. |
| 2011/0077490 A1 | 3/2011 | Simpson et al. |
| 2011/0077494 A1 | 3/2011 | Doniger et al. |
| 2011/0082484 A1 | 4/2011 | Saravia et al. |
| 2011/0097090 A1 | 4/2011 | Cao |
| 2011/0106126 A1 | 5/2011 | Love et al. |
| 2011/0112696 A1 | 5/2011 | Yodfat et al. |
| 2011/0148905 A1 | 6/2011 | Simmons et al. |
| 2011/0190603 A1 | 8/2011 | Stafford |
| 2011/0191044 A1 | 8/2011 | Stafford |
| 2011/0208027 A1 | 8/2011 | Wagner et al. |
| 2011/0213225 A1 | 9/2011 | Bernstein et al. |

(56) References Cited

U.S. PATENT DOCUMENTS

| | | |
|---|---|---|
| 2011/0257495 A1 | 10/2011 | Hoss et al. |
| 2011/0257895 A1 | 10/2011 | Brauker et al. |
| 2011/0263958 A1 | 10/2011 | Brauker et al. |
| 2011/0282327 A1 | 11/2011 | Kellogg et al. |
| 2011/0287528 A1 | 11/2011 | Fern et al. |
| 2011/0288574 A1 | 11/2011 | Curry et al. |
| 2011/0289497 A1 | 11/2011 | Kiaie et al. |
| 2011/0319729 A1 | 12/2011 | Donnay et al. |
| 2011/0320130 A1 | 12/2011 | Valdes et al. |
| 2011/0320167 A1 | 12/2011 | Budiman |
| 2012/0010642 A1 | 1/2012 | Lee et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0173200 A1 | 7/2012 | Breton et al. |
| 2012/0190989 A1 | 7/2012 | Kaiser et al. |
| 2012/0226121 A1 | 9/2012 | Kamath et al. |
| 2013/0035575 A1 | 2/2013 | Mayou et al. |
| 2013/0225959 A1 | 8/2013 | Bugler |
| 2013/0231541 A1 | 9/2013 | Hayter et al. |
| 2013/0235166 A1 | 9/2013 | Jones et al. |
| 2013/0324823 A1 | 12/2013 | Koski et al. |
| 2014/0005499 A1 | 1/2014 | Catt et al. |
| 2014/0046160 A1 | 2/2014 | Terashima et al. |
| 2015/0241407 A1 | 8/2015 | Ou et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 2335584 | 6/2011 |
| JP | 2003-503090 | 1/2003 |
| JP | 2004-520898 | 7/2004 |
| JP | 2005-265838 | 9/2005 |
| JP | 2007-040963 | 2/2007 |
| JP | 2008-506468 | 3/2008 |
| JP | 2011-505834 | 3/2011 |
| WO | WO-1996/025089 | 8/1996 |
| WO | WO-1996/035370 | 11/1996 |
| WO | WO-1999/060391 | 11/1999 |
| WO | WO-2000/049940 | 8/2000 |
| WO | WO-2000/059370 | 10/2000 |
| WO | WO-2001/052935 | 7/2001 |
| WO | WO-2001/054753 | 8/2001 |
| WO | WO-2002/016905 | 2/2002 |
| WO | WO-2003/076893 | 9/2003 |
| WO | WO-2003/082091 | 10/2003 |
| WO | WO-2006/024671 | 3/2006 |
| WO | WO-2006/085087 | 8/2006 |

OTHER PUBLICATIONS

European Patent Application No. 10802926.5, Examination Report dated Dec. 22, 2017.

Armour, J. C., et al., "Application of Chronic Intravascular Blood Glucose Sensor in Dogs", *Diabetes*, vol. 39, 1990, pp. 1519-1526.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Bremer, T. M., et al., "Benchmark Data from the Literature for Evaluation of New Glucose Sensing Technologies", *Diabetes Technology & Therapeutics*, vol. 3, No. 3, 2001, pp. 409-418.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56 No. 4, 1984, 667-671.

Cheyne, E. H., et al., "Performance of a Continuous Glucose Monitoring System During Controlled Hypoglycaemia in Healthy Volunteers", *Diabetes Technology & Therapeutics*, vol. 4, No. 5, 2002, pp. 607-613.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Jobst, G., et al., "Thin-Film Microbiosensors for Glucose-Lactate Monitoring", *Analytical Chemistry*, vol. 68, No. 18, 1996, pp. 3173-3179.

Johnson, P. C., "Peripheral Circulation", John Wiley & Sons, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Kuure-Kinsey, M., et al., "A Dual-Rate Kalman Filter for Continuous Glucose Monitoring", *Proceedings of the 28th IEEE, EMBS Annual International Conference*, New York City, Aug. 30 to Sep. 3, 2006, pp. 63-66.

Lodwig, V., et al., "Continuous Glucose Monitoring with Glucose Sensors: Calibration and Assessment Criteria", *Diabetes Technology & Therapeutics*, vol. 5, No. 4, 2003, pp. 573-587.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

Mcgarraugh, G., et al., "Glucose Measurements Using Blood Extracted from the Forearm and the Finger", TheraSense, Inc., 2001, 16 Pages.

Mcgarraugh, G., et al., "Physiological Influences on Off-Finger Glucose Testing", *Diabetes Technology & Therapeutics*, vol. 3, No. 3, 2001, pp. 367-376.

Mckean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Morbiducci, U, et al., "Improved Usability of the Minimal Model of Insulin Sensitivity Based on an Automated Approach and Genetic Algorithms for Parameter Estimation", *Clinical Science*, vol. 112, Feb. 2007, pp. 257-263.

Mougiakakou, et al., "A Real Time Simulation Model of Glucose-Insulin Metabolism for Type 1 Diabetes Patients", *Proceedings of the 2005 IEEE*, 2005, pp. 298-301.

(56) References Cited

OTHER PUBLICATIONS

Panteleon, A. E., et al., "The Role of the Independent Variable to Glucose Sensor Calibration", *Diabetes Technology & Therapeutics*, vol. 5, No. 3, 2003, pp. 401-410.
Parker, R., et al., "Robust H∞ Glucose Control in Diabetes Using a Physiological Model", *AIChE Journal*, vol. 46, No. 12, 2000, pp. 2537-2549.
Pickup, J., et al., "Implantable Glucose Sensors: Choosing the Appropriate Sensing Strategy", *Biosensors*, vol. 3, 1987/88, pp. 335-346.
Pickup, J., et al., "In Vivo Molecular Sensing in Diabetes Mellitus: An Implantable Glucose Sensor with Direct Electron Transfer", *Diabetologia*, vol. 32, 1989, pp. 213-217.
Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.
Quinn, C. P., et al., "Kinetics of Glucose Delivery to Subcutaneous Tissue in Rats Measured with 0.3-mm Amperometric Microsensors", *The American Physiological Society*, 1995, E155-E161.
Roe, J. N., et al., "Bloodless Glucose Measurements", *Critical Review in Therapeutic Drug Carrier Systems*, vol. 15, Issue 3, 1998, pp. 199-241.
Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.
Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.
Salehi, C., et al., "A Telemetry-Instrumentation System for Long-Term Implantable Glucose and Oxygen Sensors", *Analytical Letters*, vol. 29, No. 13, 1996, pp. 2289-2308.
Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.
Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.
Shichiri, M., et al., "Glycaemic Control in Pancreatectomized Dogs with a Wearable Artificial Endocrine Pancreas", *Diabetologia*, vol. 24, 1983, pp. 179-184.
Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.
Shichiri, M., et al., "Membrane Design for Extending the Long-Life of an Implantable Glucose Sensor", *Diabetes Nutrition and Metabolism*, vol. 2, 1989, pp. 309-313.
Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.
Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.
Shichiri, M., et al., "Wearable Artificial Endocrine Pancreas With Needle-Type Glucose Sensor", *The Lancet*, 1982, pp. 1129-1131.
Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.
Chinese Patent Application No. 201080018303.6, Original Language and English Translation of Office Action dated Jan. 22, 2014.
Chinese Patent Application No. 201080018303.6, Original Language and English Translation of Office Action dated Jul. 29, 2013.
Chinese Patent Application No. 201080033422.9, Original Language and English Translation of Office Action dated Jun. 9, 2014.
Chinese Patent Application No. 201080033422.9, Original Language and English Translation of Office Action dated Oct. 25, 2013.
Chinese Patent Application No. 201080033422.9, Original Language and English Translation of Office Action dated Sep. 12, 2014.
European Patent Application No. 10746954.6, Extended European Search Report dated Jun. 3, 2014.
European Patent Application No. 10802926.5, Extended European Search Report dated Jun. 3, 2014.
Japanese Patent Application No. 2011-552211, Original Language and English Translation of Decision of Rejection dated Mar. 3, 2015.
Japanese Patent Application No. 2011-552211, Original Language and English Translation of Office Action dated May 27, 2014.
PCT Application No. PCT/US2010/025693, International Preliminary Report on Patentability and Written Opinion of the International Searching Authority dated Sep. 9, 2011.
PCT Application No. PCT/US2010/025693, International Search Report and Written Opinion of the International Searching Authority dated May 12, 2010.
PCT Application No. PCT/US2010/042974, International Preliminary Report on Patentability and Written Opinion of the International Searching Authority dated Feb. 2, 2012.
PCT Application No. PCT/US2010/042974, International Search Report and Written Opinion of the International Searching Authority dated Sep. 15, 2010.
U.S. Appl. No. 12/714,439, Office Action dated Jan. 20, 2016.
U.S. Appl. No. 12/714,439, Office Action dated Jul. 7, 2015.
U.S. Appl. No. 12/714,439, Office Action dated Mar. 1, 2013.
U.S. Appl. No. 12/714,439, Office Action dated Nov. 21, 2013.
U.S. Appl. No. 12/714,439, Office Action dated Sep. 29, 2016.
U.S. Appl. No. 12/842,013, Advisory Action dated Dec. 3, 2015.
U.S. Appl. No. 12/842,013, Advisory Action dated May 5, 2014.
U.S. Appl. No. 12/842,013, Notice of Allowance dated Aug. 22, 2017.
U.S. Appl. No. 12/842,013, Office Action dated Aug. 26, 2015.
U.S. Appl. No. 12/842,013, Office Action dated Feb. 25, 2014.
U.S. Appl. No. 12/842,013, Office Action dated Feb. 7, 2013.
U.S. Appl. No. 12/842,013, Office Action dated Mar. 23, 2016.
U.S. Appl. No. 12/842,013, Office Action dated Nov. 6, 2014.
U.S. Appl. No. 12/842,013, Office Action dated Oct. 28, 2013.
U.S. Appl. No. 12/842,013, Office Action dated Sep. 1, 2016.
U.S. Appl. No. 14/490,519, Office Action dated Feb. 11, 2015.
Extended European Search Report dated May 6, 2020 in Application No. EP 19214506.

* cited by examiner

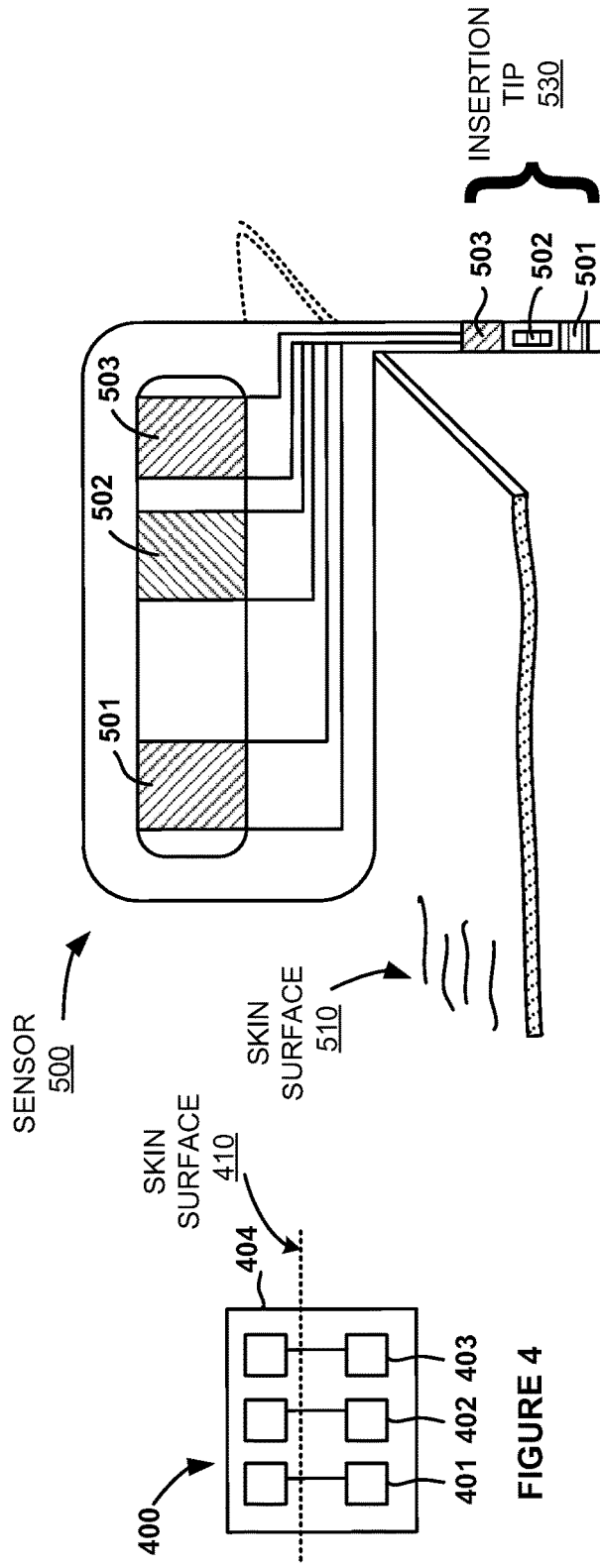
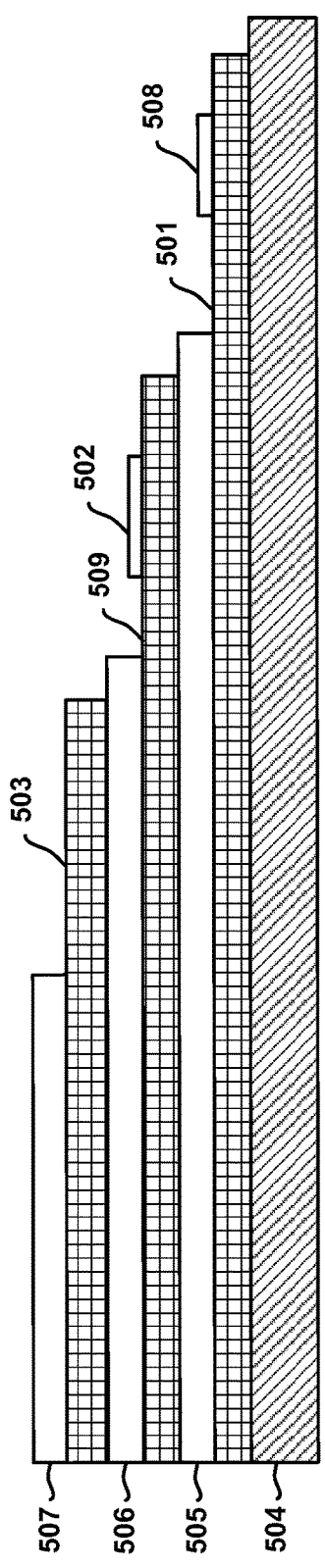

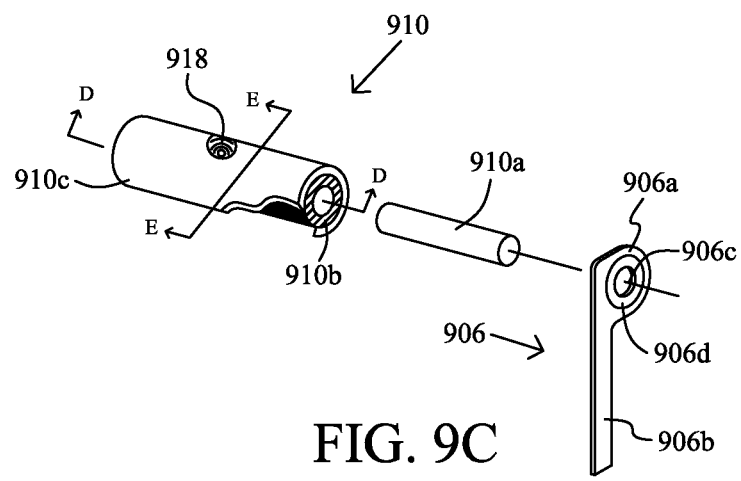
FIG. 9C
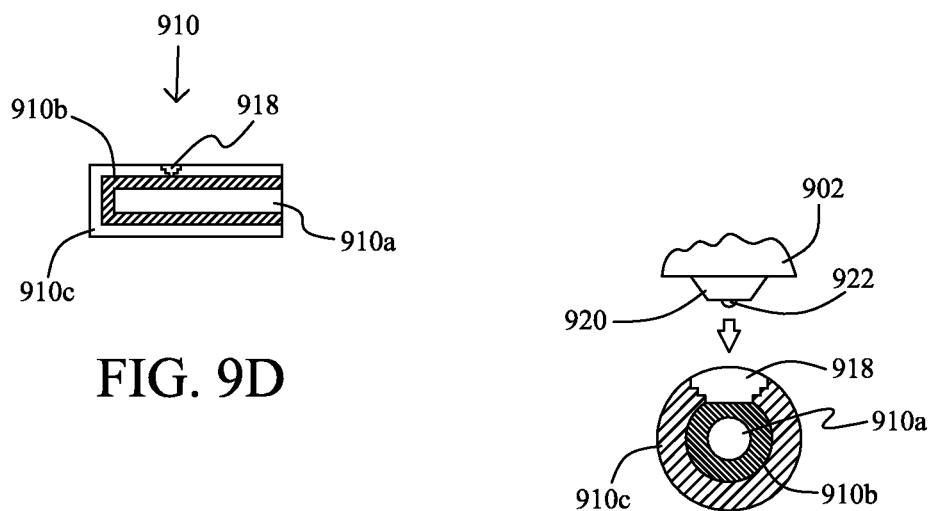
FIG. 9D
FIG. 9E

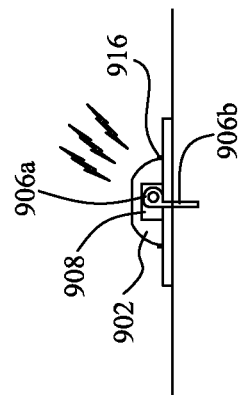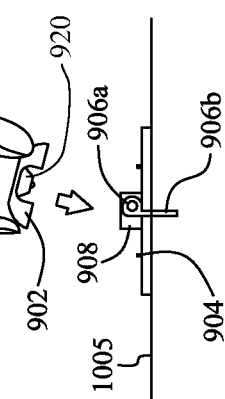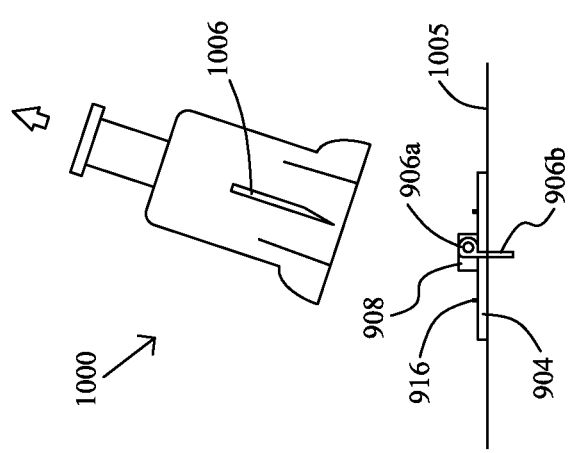

CONTINUOUS ANALYTE MEASUREMENT SYSTEMS AND SYSTEMS AND METHODS FOR IMPLANTING THEM

RELATED APPLICATION

The present application is a continuation of U.S. patent application Ser. No. 12/842,013 filed Jul. 22, 2010, now U.S. Pat. No. 9,795,326, which claims priority under 35 U.S.C. § 119(e) to U.S. Provisional Application No. 61/227,967 filed Jul. 23, 2009, entitled "Continuous Analyte Measurement Systems and Systems and Methods for Implanting Them", the disclosures of each of which are incorporated herein by reference for all purposes.

BACKGROUND

There are a number of instances when it is desirable or necessary to monitor the concentration of an analyte, such as glucose, lactate, or oxygen, for example, in bodily fluid of a body. For example, it may be desirable to monitor high or low levels of glucose in blood or other bodily fluid that may be detrimental to a human. In a healthy human, the concentration of glucose in the blood is maintained between about 0.8 and about 1.2 mg/mL by a variety of hormones, such as insulin and glucagons, for example. If the blood glucose level is raised above its normal level, hyperglycemia develops and attendant symptoms may result. If the blood glucose concentration falls below its normal level, hypoglycemia develops and attendant symptoms, such as neurological and other symptoms, may result. Both hyperglycemia and hypoglycemia may result in death if untreated. Maintaining blood glucose at an appropriate concentration is thus a desirable or necessary part of treating a person who is physiologically unable to do so unaided, such as a person who is afflicted with diabetes mellitus.

Certain compounds may be administered to increase or decrease the concentration of blood glucose in a body. By way of example, insulin can be administered to a person in a variety of ways, such as through injection, for example, to decrease that person's blood glucose concentration. Further by way of example, glucose may be administered to a person in a variety of ways, such as directly, through injection or administration of an intravenous solution, for example, or indirectly, through ingestion of certain foods or drinks, for example, to increase that person's blood glucose level.

Regardless of the type of adjustment used, it is typically desirable or necessary to determine a person's blood glucose concentration before making an appropriate adjustment. Typically, blood glucose concentration is monitored by a person or sometimes by a physician using an in vitro test that requires a blood sample. The person may obtain the blood sample by withdrawing blood from a blood source in his or her body, such as a vein, using a needle and syringe, for example, or by lancing a portion of his or her skin, using a lancing device, for example, to make blood available external to the skin, to obtain the necessary sample volume for in vitro testing. The fresh blood sample is then applied to an in vitro testing device such as an analyte test strip, whereupon suitable detection methods, such as colorimetric, electrochemical, or photometric detection methods, for example, may be used to determine the person's actual blood glucose level. The foregoing procedure provides a blood glucose concentration for a particular or discrete point in time, and thus, must be repeated periodically, in order to monitor blood glucose over a longer period.

Conventionally, a "finger stick" is generally performed to extract an adequate volume of blood from a finger for in vitro glucose testing since the tissue of the fingertip is highly perfused with blood vessels. These tests monitor glucose at discrete periods of time when an individual affirmatively initiates a test at a given point in time, and therefore may be characterized as "discrete" tests. Unfortunately, the fingertip is also densely supplied with pain receptors, which can lead to significant discomfort during the blood extraction process. Unfortunately, the consistency with which the level of glucose is checked varies widely among individuals. Many diabetics find the periodic testing inconvenient and they sometimes forget to test their glucose level or do not have time for a proper test. Further, as the fingertip is densely supplied with pain receptors which causes significant discomfort during the blood extraction process, some individuals will not be inclined to test their glucose levels as frequently as they should. These situations may result in hyperglycemic or hypoglycemic episodes.

Glucose monitoring systems that allow for sample extraction from sites other than the finger and/or that can operate using small samples of blood, have been developed. (See, e.g., U.S. Pat. Nos. 6,120,676, 6,591,125 and 7,299,082, the disclosures of each of which are incorporated herein by reference for all purposes). Typically, about one µL or less of sample may be required for the proper operation of these devices, which enables glucose testing with a sample of blood obtained from the surface of a palm, a hand, an arm, a thigh, a leg, the torso, or the abdomen. Even though less painful than the finger stick approach, these other sample extraction methods are still inconvenient and may also be somewhat painful.

In addition to the discrete, in vitro, blood glucose monitoring systems described above, at least partially implantable, or in vivo, blood glucose monitoring systems, which are designed to provide continuous or semi-continuous in vivo measurement of an individual's glucose concentration, have been described. See, e.g., U.S. Pat. Nos. 6,175,752, 6,284,478, 6,134,461, 6,560,471, 6,746,582, 6,579,690, 6,932,892 and 7,299,082, the disclosures of each of which are incorporated herein by reference for all purposes.

A number of these in vivo systems are based on "enzyme electrode" technology, whereby an enzymatic reaction involving an enzyme such as glucose oxidase, glucose dehydrogenase, or the like, is combined with an electrochemical sensor for the determination of an individual's glucose level in a sample of the individual's biological fluid. By way of example, the electrochemical sensor may be placed in substantially continuous contact with a blood source, e.g., may be inserted into a blood source, such as a vein or other blood vessel, for example, such that the sensor is in continuous contact with blood and can effectively monitor blood glucose levels. Further by way of example, the electrochemical sensor may be placed in substantially continuous contact with bodily fluid other than blood, such as dermal or subcutaneous fluid, for example, for effective monitoring of glucose levels in such bodily fluid, such as interstitial fluid.

Relative to discrete or periodic monitoring using analyte test strips, continuous monitoring is generally more desirable in that it may provide a more comprehensive assessment of glucose levels and more useful information, including predictive trend information, for example. Subcutaneous continuous glucose monitoring is also desirable as it is typically less invasive than continuous glucose monitoring in blood accessed from a blood vessel.

Regardless of the type of implantable analyte monitoring device employed, it has been observed that transient, low sensor readings which result in clinically significant sensor related errors may occur for a period of time. For example, it has been found that during the initial 12-24 hours of sensor operation (after implantation), a glucose sensor's sensitivity (defined as the ratio between the analyte sensor current level and the blood glucose level) may be relatively low—a phenomenon sometimes referred to as "early signal attenuation" (ESA). Additionally, low sensor readings may be more likely to occur at certain predictable times such as during night time use—commonly referred to as "night time drop outs". An in vivo analyte sensor with lower than normal sensitivity may report blood glucose values lower than the actual values, thus potentially underestimating hyperglycemia, and triggering false hypoglycemia alarms.

While these transient, low readings are infrequent and, in many instances, resolve after a period of time, the negative deviations in sensor readings impose constraints upon analyte monitoring during the period in which the deviations are observed. One manner of addressing this problem is to configure the analyte monitoring system so as to delay reporting readings to the user until after this period of negative deviations passes. However, this leaves the user vulnerable and relying on alternate means of analyte measuring, e.g., in vitro testing, during this time. Another way of addressing negative deviations in sensor sensitivity is to require frequent calibration of the sensor during the time period in which the sensor is used. This is often accomplished in the context of continuous glucose monitoring devices by using a reference value after the sensor has been positioned in the body, where the reference value most often employed is obtained by a finger stick and use of a blood glucose test strip. However, these multiple calibrations are not desirable for at least the reasons that they are inconvenient and painful, as described above.

One cause of spurious low readings or drop outs by these implantable sensors is thought to be the presence of blood clots, also known as "thrombi", formed as a result of insertion of the sensor in vivo. Such clots exist in close proximity to a subcutaneous glucose sensor and have a tendency to "consume" glucose at a high rate, thereby lowering the local glucose concentration. It may also be that the implanted sensor constricts adjacent blood vessels thereby restricting glucose delivery to the sensor site.

One approach to addressing the problem of drop outs is to reduce the size of the sensor, thereby reducing the likelihood of thrombus formation upon implantation and impingement of the sensor structure on adjacent blood vessels, and thus, maximizing fluid flow to the sensor. One manner of reducing the size or surface area of at least the implantable portion of a sensor is to provide a sensor in which the sensor's electrodes and other sensing components and/or layers are distributed over both sides of the sensor, thereby necessitating a narrow sensor profile. Examples of such double-sided sensors are disclosed in U.S. Pat. No. 6,175,752, U.S. Patent Application Publication No. 2007/0203407, now U.S. Pat. No. 7,826,879, and U.S. Provisional Application No. 61/165,499 filed Mar. 31, 2009, the disclosures of each of which are incorporated herein by reference for all purposes.

It would also be desirable to provide sensors for use in a continuous analyte monitoring system that have negligible variations in sensitivity, including no variations or at least no statistically significant and/or clinically significant variations, from sensor to sensor. Such sensors would have to lend themselves to being highly reproducible and would necessarily involve the use of extremely accurate fabrication processes.

It would also be highly advantageous to provide continuous analyte monitoring systems that are substantially impervious to, or at least minimize, spurious low readings due to the in vivo environmental effects of subcutaneous implantation, such as ESA and night-time dropouts. Of particular interest are analyte monitoring devices and systems that are capable of substantially immediate and accurate analyte reporting to the user so that spurious low readings, or frequent calibrations, are minimized or are non existent.

It would also be highly advantageous if such sensors had a construct which makes them even less invasive than currently available sensors and which further minimizes pain and discomfort to the user.

SUMMARY

Embodiments of the present disclosure include continuous analyte monitoring systems utilizing implantable or partially implantable analyte sensors which have a relatively small profile (as compared to currently available implantable sensors). The relatively small size of the subject sensors reduce the likelihood of bleeding and, therefore, minimize thrombus formation upon implantation and the impingement of the sensor structure on adjacent blood vessels, and thus, maximizing fluid flow to the sensor and reducing the probability of ESA or low sensor readings.

In certain embodiments, the sensors are double-sided, meaning that both sides of the sensor's substrate are electrochemically functional, i.e., each side provides at least one electrode, thereby reducing the necessary surface area of the sensor. This enables the sensors to have a relatively smaller insertable distal or tail portion which reduces the in vivo environmental effects to which they are subjected. Further, the non-insertable proximal or external portion of the sensor may also have a relatively reduced size.

The subject continuous analyte monitoring systems include a skin-mounted portion or assembly and a remote portion or assembly. The skin-mounted portion includes at least the data transmitter, the transmitter battery, a portion of the sensor electronics, and electrical contacts for electrically coupling the implanted sensor with the transmitter. The remote portion of the system includes at least a data receiver and a user interface which may also be configured for test strip-based glucose monitoring. The skin-mounted portion of the system has a housing or base which is constructed to externally mount to the patient's skin and to mechanically and electrically couple the implanted sensor with the transmitter. Removably held or positioned within the housing/base structure is a connector piece having an electrical contact configuration which, when used with a double-sided sensor, enables coupling of the sensor to the transmitter in a low-profile, space-efficient manner. The skin-mounted components of the system, including the associated mounting/coupling structure, have complementary diminutive structures which, along with the very small sensor, which maximize patient usability and comfort.

Embodiments further include systems and devices for implanting the subject analyte sensors within a patient's skin and simultaneously coupling the analyte monitoring system's external, skin-mounted unit to the implanted sensor. Certain insertion systems include at least a manually-held and/or manually-operated inserter device and an insertion needle which is carried by and removably coupled to the inserter. In certain of these embodiments, only the insertion needle is disposable with the inserter or insertion gun being reusable, reducing the overall cost of the system and providing environmental advantages. In other embodiments, the skin-mounted unit and sensor are inserted manually without the use of an insertion device.

Embodiments of the subject continuous analyte monitoring systems may include additional features and advantages. For example, certain embodiments do not require individual-specific calibration by the user, and, in certain of these embodiments, require no factory-based calibration as well. Certain other embodiments of the continuous analyte monitoring systems are capable of substantially immediate and accurate analyte reporting to the user so that spurious low readings, or frequent calibrations, are minimized or are non-existent.

The subject analyte sensors usable with the subject continuous analyte monitoring systems are highly reproducible with negligible or virtually non-existent sensor-to-sensor variations with respect to sensitivity to the analyte, eliminating the need for user-based calibration. Furthermore, in certain embodiments, the analyte sensors have a predictable sensitivity drift on the shelf and/or during in vivo use are provided. Computer programmable products including devices and/or systems that include programming for a given sensor drift profile may also be provided. The programming may use the drift profile to apply a correction factor to the system to eliminate the need for user-based calibration.

These and other features, objects and advantages of the present disclosure will become apparent to those persons skilled in the art upon reading the details of the present disclosure as more fully described below.

INCORPORATION BY REFERENCE

The following patents, applications and/or publications are incorporated herein by reference for all purposes: U.S. Pat. Nos. 4,545,382; 4,711,245; 5,262,035; 5,262,305; 5,264,104; 5,320,715; 5,356,786; 5,509,410; 5,543,326; 5,593,852; 5,601,435; 5,628,890; 5,820,551; 5,822,715; 5,899,855; 5,918,603; 6,071,391; 6,103,033; 6,120,676; 6,121,009; 6,134,461; 6,143,164; 6,144,837; 6,161,095; 6,175,752; 6,270,455; 6,284,478; 6,299,757; 6,338,790; 6,377,894; 6,461,496; 6,503,381; 6,514,460; 6,514,718; 6,540,891; 6,560,471; 6,579,690; 6,591,125; 6,592,745; 6,600,997; 6,605,200; 6,605,201; 6,616,819; 6,618,934; 6,650,471; 6,654,625; 6,676,816; 6,730,200; 6,736,957; 6,746,582; 6,749,740; 6,764,581; 6,773,671; 6,881,551; 6,893,545; 6,932,892; 6,932,894; 6,942,518; 7,041,468; 7,167,818; and 7,299,082; U.S. Published Application Nos. 2004/0186365, now U.S. Pat. No. 7,811,231; 2005/0182306, now U.S. Pat. No. 8,771,183; 2006/0025662, now U.S. Pat. No. 7,740,581; 2006/0091006; 2007/0056858, now U.S. Pat. No. 8,298,389; 2007/0068807, now U.S. Pat. No. 7,846, 311; 2007/0095661; 2007/0108048, now U.S. Pat. No. 7,918,975; 2007/0199818, now U.S. Pat. No. 7,811,430; 2007/0227911, now U.S. Pat. No. 7,887,682; 2007/0233013; 2008/0066305, now U.S. Pat. No. 7,895,740; 2008/0081977, now U.S. Pat. No. 7,618,369; 2008/0102441, now U.S. Pat. No. 7,822,557; 2008/0148873, now U.S. Pat. No. 7,802,467; 2008/0161666; 2008/0267823; and 2009/0054748, now U.S. Pat. No. 7,885,698; U.S. patent application Ser. No. 11/461,725, now U.S. Pat. No. 7,866, 026; Ser. No. 12/131,012; 12/242,823, now U.S. Pat. No. 8,219,173; Ser. No. 12/363,712, now U.S. Pat. No. 8,346, 335; Ser. No. 12/495,709; 12/698,124; and Ser. No. 12/714, 439; U.S. Provisional Application Ser. Nos. 61/184,234; 61/230,686; and 61/347,754.

BRIEF DESCRIPTION OF THE DRAWINGS

A detailed description of various aspects, features and embodiments of the present disclosure is provided herein with reference to the accompanying drawings, which are briefly described below. The drawings are illustrative and are not necessarily drawn to scale, with some components and features being exaggerated for clarity. The drawings illustrate various aspects and features of the present disclosure and may illustrate one or more embodiment(s) or example(s) of the present disclosure in whole or in part. A reference numeral, letter, and/or symbol that is used in one drawing to refer to a particular element or feature maybe used in another drawing to refer to a like element or feature. Included in the drawings are the following:

FIG. 4 shows a schematic diagram of an embodiment of an analyte sensor usable with the present disclosure;

FIGS. 5A and 5B show perspective and cross sectional views, respectively, of an embodiment of an analyte sensor usable with the present disclosure;

FIGS. 9A-9E show various views of another embodiment of a continuous analyte monitoring system of the present disclosure utilizing a different double-sided analyte sensor; specifically, FIG. 9A is a cross-sectional view of the system's control unit, including the transmitter, on-skin mounting structure, and an electrical/mechanical connector with an analyte sensor operatively attached thereto;

FIG. 9B is an exploded view of the connector and analyte sensor; FIG. 9C is an exploded, partial cutaway view of the mechanical/electrical connector and the analyte sensor; FIG. 9D is a lengthwise cross-sectional view of the cutaway portion of the connector taken along lines D-D of FIG. 9C; FIG. 9E is a cross-sectional view of the coupling core, taken along lines E-E of FIG. 9C, and associated pins of the system's transmitter;

FIGS. 10A-10F are schematic representations illustrating use of an insertion system of the present disclosure to insert the continuous analyte monitoring system of FIGS. 9A-9E on/in the skin of a patient;

10A-10F having the double-sided analyte sensor of FIGS. 9A-9E operatively nested therein.

DETAILED DESCRIPTION

Before the embodiments of the present disclosure are described, it is to be understood that the present disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within embodiments of the present disclosure. The upper and lower limits of these smaller ranges may independently be included in the smaller ranges as also encompassed within embodiments of the present disclosure, subject to any specifically excluded limit in the stated range. Where the stated range includes one or both of the limits, ranges excluding either or both of those included limits are also included in the present disclosure.

Generally, embodiments of the present disclosure relate to methods and devices for detecting at least one analyte, such as glucose, in body fluid. Embodiments relate to the continuous and/or automatic in vivo monitoring of the level of one or more analytes using a continuous analyte monitoring system that includes an analyte sensor for the in vivo detection, of an analyte, such as glucose, lactate, and the like, in a body fluid. Embodiments include wholly implantable analyte sensors and analyte sensors in which only a portion of the sensor is positioned under the skin and a portion of the sensor resides above the skin, e.g., for contact to a control unit, transmitter, receiver, transceiver, processor, etc. At least a portion of a sensor may be, for example, subcutaneously positionable in a patient for the continuous or semi-continuous monitoring of a level of an analyte in a patient's interstitial fluid. For the purposes of this description, semi-continuous monitoring and continuous monitoring will be used interchangeably, unless noted otherwise. The sensor response may be correlated and/or converted to analyte levels in blood or other fluids. In certain embodiments, an analyte sensor may be positioned in contact with interstitial fluid to detect the level of glucose, which detected glucose may be used to infer the glucose level in the patient's bloodstream. Analyte sensors may be insertable into a vein, artery, or other portion of the body containing fluid. Embodiments of the analyte sensors of the subject disclosure may be configured for monitoring the level of the analyte over a time period which may range from minutes, hours, days, weeks, or longer.

Figure 1:
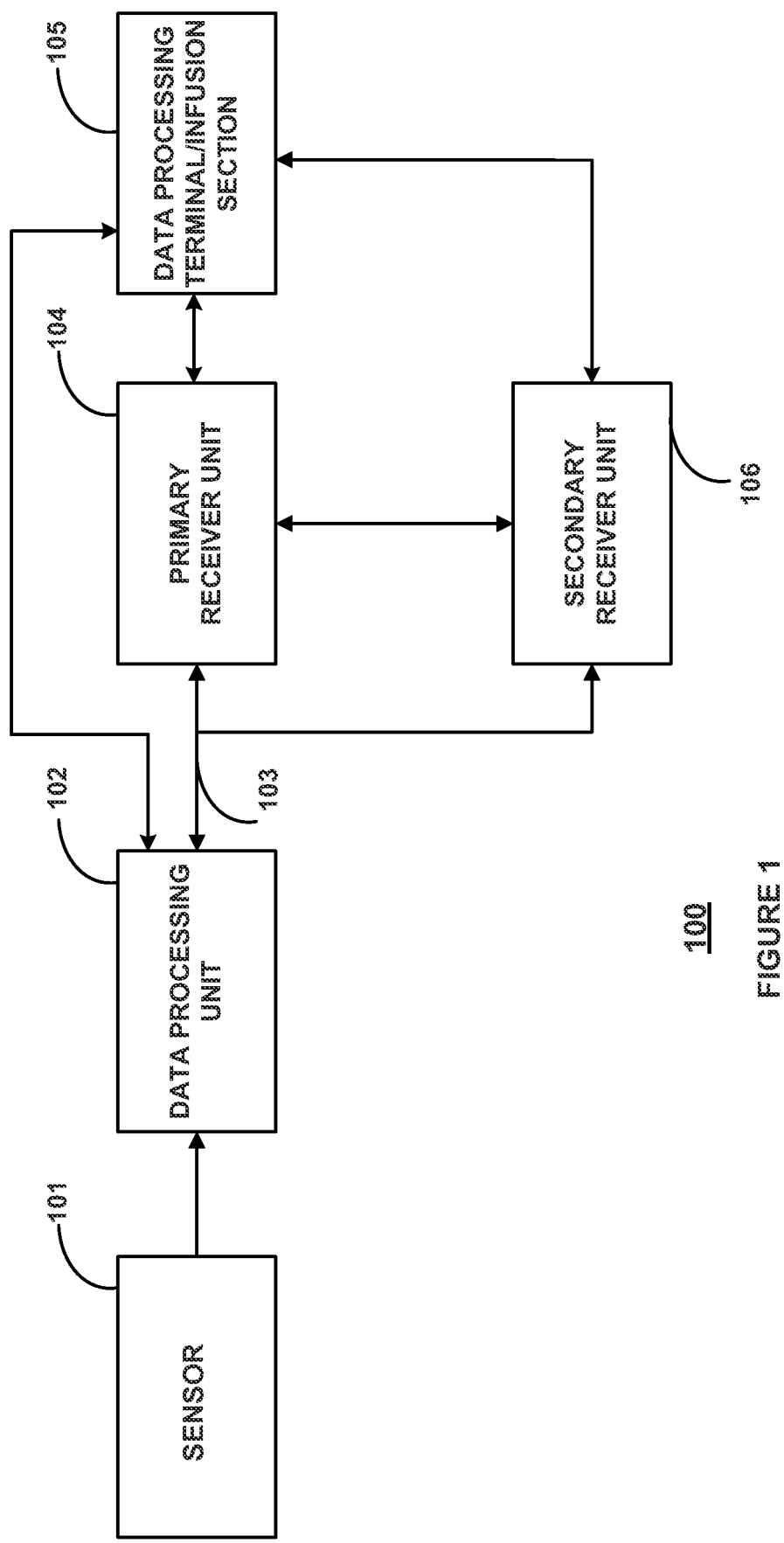
FIG. 1 shows a block diagram of an embodiment of a data monitoring and management system usable with the continuous analyte monitoring systems of the present disclosure.

FIG. 1 shows a data monitoring and management system such as, for example, an analyte (e.g., glucose) monitoring system 100 in accordance with certain embodiments. Embodiments of the subject disclosure are further described primarily with respect to glucose monitoring devices and systems, and methods of glucose detection, for convenience only and such description is in no way intended to limit the scope of the present disclosure. It is to be understood that the analyte monitoring system may be configured to monitor a variety of analytes instead of or in addition to glucose, e.g., at the same time or at different times.

Analytes that may be monitored include, but are not limited to, acetyl choline, amylase, bilirubin, cholesterol, chorionic gonadotropin, creatine kinase (e.g., CK-MB), creatine, creatinine, DNA, fructosamine, glucose, glutamine, growth hormones, hormones, ketone bodies, lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In those embodiments that monitor more than one analyte, the analytes may be monitored at the same or different times.

The analyte monitoring system 100 includes a sensor 101, a data processing unit 102 connectable to the sensor 101, and a primary receiver unit 104 which is configured to communicate with the data processing unit 102 via a communication link 103. In certain embodiments, the primary receiver unit 104 may be further configured to transmit data to a data processing terminal 105 to evaluate or otherwise process or format data received by the primary receiver unit 104. The data processing terminal 105 may be configured to receive data directly from the data processing unit 102 via a communication link which may optionally be configured for bi-directional communication. Further, the data processing unit 102 may include a transmitter or a transceiver to transmit and/or receive data to and/or from the primary receiver unit 104 and/or the data processing terminal 105 and/or optionally the secondary receiver unit 106.

Also shown in FIG. 1 is an optional secondary receiver unit 106 which is operatively coupled to the communication link 103 and configured to receive data transmitted from the data processing unit 102. The secondary receiver unit 106 may be configured to communicate with the primary receiver unit 104, as well as the data processing terminal 105. The secondary receiver unit 106 may be configured for bi-directional wireless communication with each of the primary receiver unit 104 and the data processing terminal 105. As discussed in further detail below, in certain embodiments the secondary receiver unit 106 may be a de-featured receiver as compared to the primary receiver, i.e., the secondary receiver may include a limited or minimal number of functions and features as compared with the primary receiver unit 104. As such, the secondary receiver unit 106 may include a smaller (in one or more, including all, dimensions), compact housing or embodied in a device such as a wrist watch, arm band, etc., for example. Alternatively, the secondary receiver unit 106 may be configured with the same or substantially similar functions and features as the primary receiver unit 104. The secondary receiver unit 106 may include a docking portion to be mated with a docking cradle unit for placement by, e.g., the bedside for nighttime monitoring, and/or a bi-directional communication device. A docking cradle may recharge a powers supply.

Only one sensor 101, data processing unit 102 and data processing terminal 105 are shown in the embodiment of the analyte monitoring system 100 illustrated in FIG. 1. However, it will be appreciated by one of ordinary skill in the art that the analyte monitoring system 100 may include more than one sensor 101 and/or more than one data processing unit 102, and/or more than one data processing terminal 105. Multiple sensors may be positioned in a patient for analyte monitoring at the same or different times. In certain embodiments, analyte information obtained by a first positioned sensor may be employed as a comparison to analyte information obtained by a second sensor. This may be useful to confirm or validate analyte information obtained from one or both of the sensors. Such redundancy may be useful if analyte information is contemplated in critical therapy-related decisions.

The analyte monitoring system 100 may be a continuous monitoring system or semi-continuous. In a multi-component environment, each component may be configured to be uniquely identified by one or more of the other components in the system so that communication conflict may be readily resolved between the various components within the analyte monitoring system 100. For example, unique IDs, communication channels, and the like, may be used.

In certain embodiments, the sensor 101 is physically positioned in and/or on the body of a user whose analyte level is being monitored. The sensor 101 may be configured to continuously or semi-continuously sample the analyte level of the user automatically (without the user initiating the sampling), based on a programmed intervals such as, for example, but not limited to, once every minute, once every five minutes and so on, and convert the sampled analyte level into a corresponding signal for transmission by the data processing unit 102. The data processing unit 102 is coupleable to the sensor 101 so that both devices are positioned in or on the user's body, with at least a portion of the analyte sensor 101 positioned transcutaneously. The data processing unit 102 may include a fixation element such as adhesive or the like to secure it to the user's body. A mount (not shown) attachable to the user and mateable with the unit 102 may be used. For example, a mount may include an adhesive surface. The data processing unit 102 performs data processing functions, where such functions may include, but are not limited to, filtering and encoding of data signals, each of which corresponds to a sampled analyte level of the user, for transmission to the primary receiver unit 104 via the communication link 103. In one embodiment, the sensor 101 or the data processing unit 102 or a combined sensor/data processing unit may be wholly implantable under the skin layer of the user.

In certain embodiments, the primary receiver unit 104 may include a signal interface section including an radio frequency (RF) receiver and an antenna that is configured to communicate with the data processing unit 102 via the communication link 103, and a data processing section for processing the received data from the data processing unit 102 such as data decoding, error detection and correction, data clock generation, data bit recovery, etc., or any combination thereof.

In operation, the primary receiver unit 104 in certain embodiments is configured to synchronize with the data processing unit 102 to uniquely identify the data processing unit 102, based on, for example, an identification information of the data processing unit 102, and thereafter, to continuously or semi-continuously receive signals transmitted from the data processing unit 102 associated with the monitored analyte levels detected by the sensor 101. Referring again to FIG. 1, the data processing terminal 105 may include a personal computer, a portable computer such as a laptop or a handheld device (e.g., personal digital assistants (PDAs), telephone such as a cellular phone (e.g., a multimedia and Internet-enabled mobile phone such as an iPhone or similar phone), mp3 player, pager, and the like), drug delivery device, each of which may be configured for data communication with the receiver via a wired or a wireless connection. Additionally, the data processing terminal 105 may further be connected to a data network (not shown) for storing, retrieving, updating, and/or analyzing data corresponding to the detected analyte level of the user.

The data processing terminal 105 may include an infusion device such as an insulin infusion pump or the like, which may be configured to administer insulin to patients, and which may be configured to communicate with the primary receiver unit 104 for receiving, among others, the measured analyte level. Alternatively, the primary receiver unit 104 may be configured to integrate an infusion device therein so that the primary receiver unit 104 is configured to administer insulin (or other appropriate drug) therapy to patients, for example, for administering and modifying basal profiles, as well as for determining appropriate boluses for administration based on, among others, the detected analyte levels received from the data processing unit 102. An infusion device may be an external device or an internal device (wholly implantable in a user).

In certain embodiments, the data processing terminal 105, which may include an insulin pump, may be configured to receive the analyte signals from the data processing unit 102, and thus, incorporate the functions of the primary receiver unit 104 including data processing for managing the patient's insulin therapy and analyte monitoring. In certain embodiments, the communication link 103 as well as one or more of the other communication interfaces shown in FIG. 1, may use one or more of: an RF communication protocol, an infrared communication protocol, a Bluetooth® enabled communication protocol, an 802.11x wireless communication protocol, or an equivalent wireless communication protocol which would allow secure, wireless communication of several units (for example, per HIPAA requirements), while avoiding potential data collision and interference.

Figure 2:
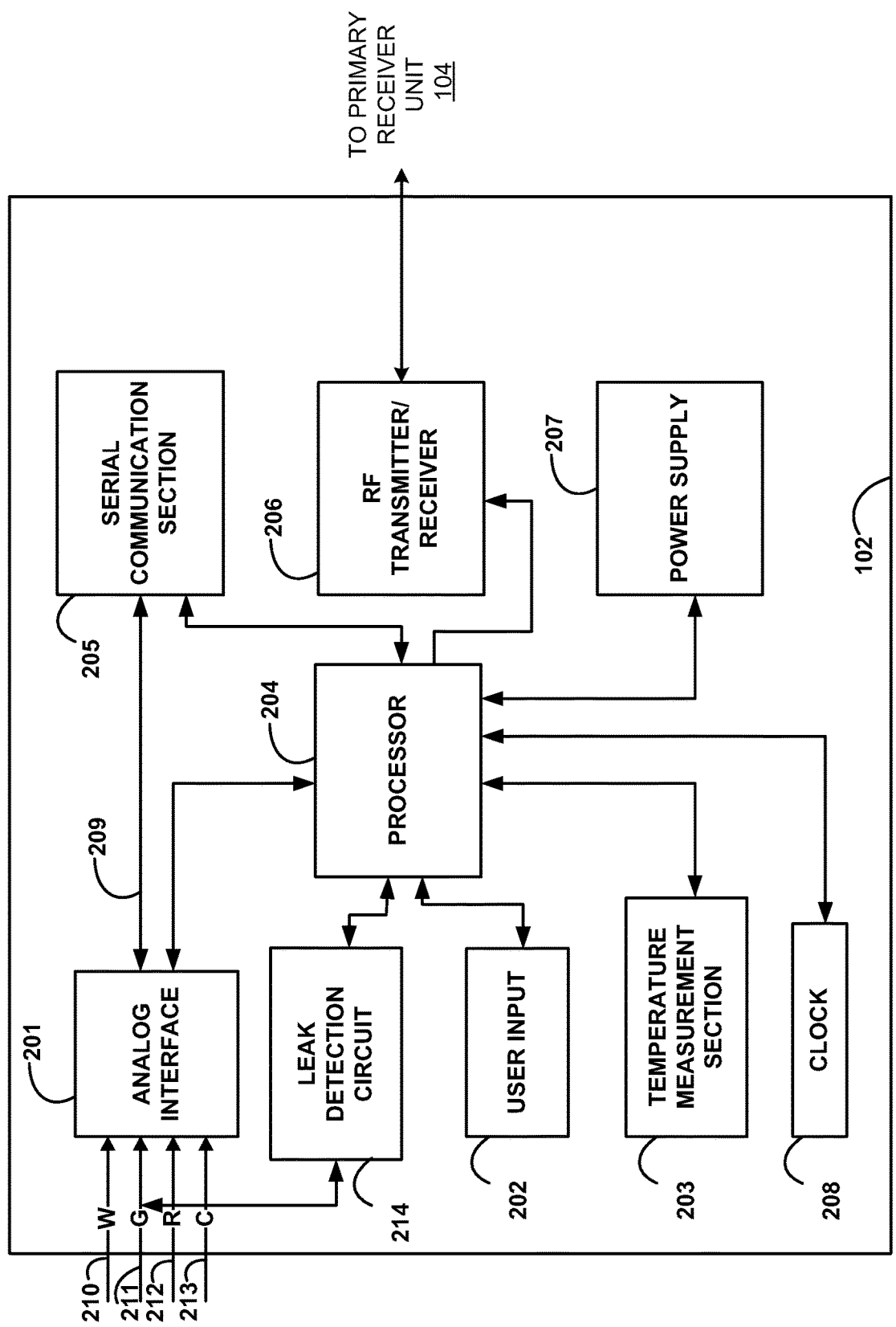
FIG. 2 shows a block diagram of an embodiment of a transmitter unit of the data monitoring and management system of FIG. 1.

FIG. 2 shows a block diagram of an embodiment of a data processing unit of the data monitoring and detection system shown in FIG. 1. User input and/or interface components may be included or a data processing unit may be free of user input and/or interface components. Referring to the Figure, the transmitter unit 102 in one embodiment includes an analog interface 201 configured to communicate with the sensor 101 (FIG. 1), a user input 202, and a temperature detection section 203, each of which is operatively coupled to a transmitter processor 204 such as a central processing unit (CPU). In certain embodiments, one or more application-specific integrated circuits (ASIC) may be used to implement one or more functions or routines associated with the operations of the data processing unit (and/or receiver unit) using for example one or more state machines and buffers.

As can be seen in the embodiment of FIG. 2, the sensor 101 (FIG. 1) includes four contacts, three of which are electrodes—work electrode (W) 210, reference electrode (R) 212, and counter electrode (C) 213, each operatively coupled to the analog interface 201 of the data processing unit 102. This embodiment also shows optional guard contact (G) 211. Fewer or greater electrodes may be employed. For example, the counter and reference electrode functions may be served by a single counter/reference electrode, there may be more than one working electrode and/or reference electrode and/or counter electrode, etc. Also shown is a leak detection circuit 214 coupled to the guard contact (G) 211 and the processor 204 in the transmitter unit 102 of the analyte monitoring system 100. The leak detection circuit 214 in accordance with one embodiment of the present disclosure may be configured to detect leakage current in the sensor 101 to determine whether the measured sensor data is corrupt or whether the measured data from the sensor 101 is accurate. Further shown in FIG. 2 are a transmitter serial communication section 205 and an RF transmitter 206, each of which is also operatively coupled to the transmitter processor 204. Moreover, a power supply 207 such as a battery is also provided in the transmitter unit 102 to provide the necessary power for the transmitter unit 102. Additionally, as can be seen from the Figure, clock 208 is provided to, among others, supply real time information to the transmitter processor 204. In one embodiment, a unidirectional input path is established from the sensor 101 (FIG. 1) and/or manufacturing and testing equipment to the analog interface 201 of the transmitter unit 102, while a unidirectional output is established from the output of the RF transmitter 206 of the transmitter unit 102 for transmission to the primary receiver unit 104. In this manner, a data path is shown in FIG. 2 between the aforementioned unidirectional input and output via a dedicated link 209 from the analog interface 201 to serial communication section 205, thereafter to the processor 204, and then to the RF transmitter 206.

Figure 3:
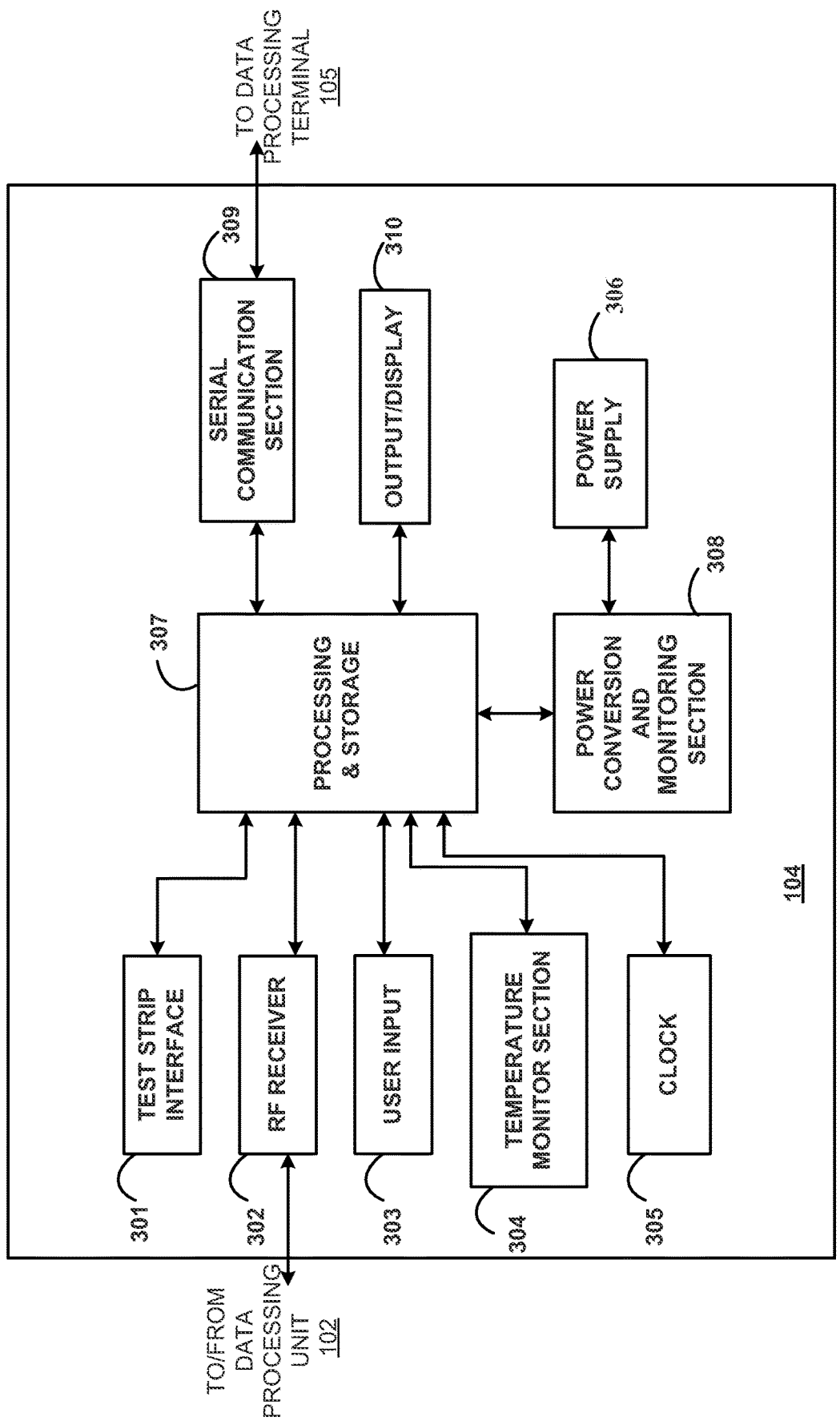
FIG. 3 shows a block diagram of an embodiment of the receiver/monitor unit of the data monitoring and management system of FIG. 1.

FIG. 3 is a block diagram of an embodiment of a receiver/monitor unit such as the primary receiver unit 104 of the data monitoring and management system shown in FIG. 1. The primary receiver unit 104 may include one or more of: a blood glucose test strip interface 301 for in vitro testing, an RF receiver 302, an input 303, a temperature monitor section 304, and a clock 305, each of which is operatively coupled to a processing and storage section 307. The primary receiver unit 104 also includes a power supply 306 operatively coupled to a power conversion and monitoring section 308. Further, the power conversion and monitoring section 308 is also coupled to the receiver processor 307. Moreover, also shown are a receiver serial communication section 309, and an output 310, each operatively coupled to the processing and storage unit 307. The receiver may include user input and/or interface components or may be free of user input and/or interface components.

In certain embodiments having a test strip interface 301, the interface includes a glucose level testing portion to receive a blood (or other body fluid sample) glucose test or information related thereto. For example, the interface may include a test strip port to receive a glucose test strip. The device may determine the glucose level of the test strip, and optionally display (or otherwise notice) the glucose level on the output 310 of the primary receiver unit 104. Any suitable test strip may be employed, e.g., test strips that only require a very small amount (e.g., one microliter or less, e.g., 0.5 microliter or less, e.g., 0.1 microliter or less), of applied sample to the strip in order to obtain accurate glucose information, e.g. Freestyle® and Precision® blood glucose test strips from Abbott Diabetes Care Inc. Glucose information obtained by the in vitro glucose testing device may be used for a variety of purposes, computations, etc. For example, the information may be used to calibrate sensor 101 (however, calibration of the subject sensors may not be necessary), confirm results of the sensor 101 to increase the confidence thereof (e.g., in instances in which information obtained by sensor 101 is employed in therapy related decisions), etc. Exemplary blood glucose monitoring systems are described, e.g., in U.S. Pat. Nos. 6,071,391, 6,120, 676, 6,338,790 and 6,616,819, and in U.S. application Ser. No. 11/282,001, now U.S. Pat. No. 7,918,975 and Ser. No. 11/225,659, now U.S. Pat. No. 8,298,389, the disclosures of each of which are incorporated herein by reference for all purposes.

In further embodiments, the data processing unit 102 and/or the primary receiver unit 104 and/or the secondary receiver unit 106, and/or the data processing terminal/infusion section 105 may be configured to receive the blood glucose value from a wired connection or wirelessly over a communication link from, for example, a blood glucose meter. In further embodiments, a user manipulating or using the analyte monitoring system 100 (FIG. 1) may manually input the blood glucose value using, for example, a user interface (for example, a keyboard, keypad, voice commands, and the like) incorporated in the one or more of the data processing unit 102, the primary receiver unit 104, secondary receiver unit 106, or the data processing terminal/infusion section 105.

Additional detailed descriptions are provided in U.S. Pat. Nos. 5,262,035, 5,262,305, 5,264,104, 5,320,715, 5,593, 852, 6,103,033, 6,134,461, 6,175,752, 6,560,471, 6,579,690, 6,605,200, 6,654,625, 6,746,582 and 6,932,894, and in U.S. Published Patent Application Nos. 2004/0186365, now U.S. Pat. No. 7,811,231 and 2005/0182306, now U.S. Pat. No. 8,771,183, the disclosures of each of which are incorporated herein by reference for all purposes.

FIG. 4 schematically shows an embodiment of an analyte sensor usable in the continuous analyte monitoring systems just described. This sensor embodiment includes electrodes 401, 402 and 403 on a base 404. Electrodes (and/or other features) may be applied or otherwise processed using any suitable technology, e.g., chemical vapor deposition (CVD), physical vapor deposition, sputtering, reactive sputtering, printing, coating, ablating (e.g., laser ablation), painting, dip coating, etching and the like. Suitable conductive materials include but are not limited to aluminum, carbon (such as graphite), cobalt, copper, gallium, gold, indium, iridium, iron, lead, magnesium, mercury (as an amalgam), nickel, niobium, osmium, palladium, platinum, rhenium, rhodium, selenium, silicon (e.g., doped polycrystalline silicon), silver, tantalum, tin, titanium, tungsten, uranium, vanadium, zinc, zirconium, mixtures thereof, and alloys, oxides, or metallic compounds of these elements.

The sensor may be wholly implantable in a user or may be configured so that only a portion is positioned within (internal) a user and another portion outside (external) a user. For example, the sensor 400 may include a portion positionable above a surface of the skin 410, and a portion positioned below the skin. In such embodiments, the external portion may include contacts (connected to respective electrodes of the second portion by traces) to connect to another device also external to the user such as a transmitter unit. While the embodiment of FIG. 4 shows three electrodes side-by-side on the same surface of base 404, other configurations are contemplated, e.g., fewer or greater electrodes, some or all electrodes on different surfaces of the base or present on another base, some or all electrodes stacked together, some or all electrodes twisted together (e.g., an electrode twisted around or about another or electrodes twisted together), electrodes of differing materials and dimensions, etc.

FIG. 5A shows a perspective view of an embodiment of an electrochemical analyte sensor 500 of the present disclosure having a first portion (which in this embodiment may be characterized as a major or body portion) positionable above a surface of the skin 510, and a second portion (which in this embodiment may be characterized as a minor or tail portion) that includes an insertion tip 530 positionable below the skin, e.g., penetrating through the skin and into, e.g., the dermal space 520, in contact with the user's biofluid such as interstitial fluid. Contact portions of a working electrode 501, a reference electrode 502, and a counter electrode 503 are positioned on the portion of the sensor 500 situated above the skin surface 510. Working electrode 501, a reference electrode 502, and a counter electrode 503 are shown at the second section and particularly at the insertion tip 530. Traces may be provided from the electrode at the tip to the contact, as shown in FIG. 5A. It is to be understood that greater or fewer electrodes may be provided on a sensor. For example, a sensor may include more than one working electrode and/or the counter and reference electrodes may be a single counter/reference electrode, etc.

FIG. 5B shows a cross sectional view of a portion of the sensor 500 of FIG. 5A. The electrodes 501, 502 and 503 of the sensor 500 as well as the substrate and the dielectric layers are provided in a layered configuration or construction. For example, as shown in FIG. 5B, in one aspect, the sensor 500 (such as the sensor 101 FIG. 1), includes a substrate layer 504, and a first conducting layer 501 such as carbon, gold, etc., disposed on at least a portion of the substrate layer 504, and which may provide the working electrode. Also shown disposed on at least a portion of the first conducting layer 501 is a sensing component or layer 508, discussed in greater detail below. The area of the conducting layer covered by the sensing layer is herein referred to as the active area. A first insulation layer such as a first dielectric layer 505 is disposed or layered on at least a portion of the first conducting layer 501, and further, a second conducting layer 502 may be disposed or stacked on top of at least a portion of the first insulation layer (or dielectric layer) 505, and which may provide the reference electrode. In one aspect, conducting layer 502 may include a layer of silver/silver chloride (Ag/AgCl), gold, etc. A second insulation layer 506 such as a dielectric layer in one embodiment may be disposed or layered on at least a portion of the second conducting layer 509. Further, a third conducting layer 503 may provide the counter electrode 503. It may be disposed on at least a portion of the second insulation layer 506. Finally, a third insulation layer 507 may be disposed or layered on at least a portion of the third conducting layer 503. In this manner, the sensor 500 may be layered such that at least a portion of each of the conducting layers is separated by a respective insulation layer (for example, a dielectric layer). The embodiment of FIGS. 5A and 5B show the layers having different lengths. Some or all of the layers may have the same or different lengths and/or widths.

In addition to the electrodes, sensing layer and dielectric layers, sensor 500 may also include a temperature probe, a mass transport limiting layer, a biocompatible layer, and/or other optional components (none of which are illustrated). Each of these components enhances the functioning of and/or results from the sensor.

Substrate 504 may be formed using a variety of non-conducting materials, including, for example, polymeric or plastic materials and ceramic materials. (It is to be understood that substrate includes any dielectric material of a sensor, e.g., around and/or in between electrodes of a sensor such as a sensor in the form of a wire wherein the electrodes of the sensor are wires that are spaced-apart by a substrate). In some embodiments, the substrate is flexible. For example, if the sensor is configured for implantation into a patient, then the sensor may be made flexible (although rigid sensors may also be used for implantable sensors) to reduce pain to the patient and damage to the tissue caused by the implantation of and/or the wearing of the sensor. A flexible substrate often increases the patient's comfort and allows a wider range of activities. Suitable materials for a flexible substrate include, for example, non-conducting plastic or polymeric materials and other non-conducting, flexible, deformable materials. Examples of useful plastic or polymeric materials include thermoplastics such as polycarbonates, polyesters (e.g., Mylar and polyethylene terephthalate (PET)), polyvinyl chloride (PVC), polyurethanes, polyethers, polyamides, polyimides, or copolymers of these thermoplastics, such as PETG (glycol-modified polyethylene terephthalate).

In other embodiments, the sensors, or at least a portion of the sensors, are made using a relatively rigid substrate, for example, to provide structural support against bending or breaking. Examples of rigid materials that may be used as the substrate include poorly conducting ceramics, such as aluminum oxide and silicon dioxide. One advantage of an implantable sensor having a rigid substrate is that the sensor 500 may have a sharp point and/or a sharp edge to aid in implantation of a sensor without an additional insertion device. It will be appreciated that for many sensors and sensor applications, both rigid and flexible sensors will operate adequately. The flexibility of the sensor may also be controlled and varied along a continuum by changing, for example, the composition and/or thickness and/or width of the substrate (and/or the composition and/or thickness and/or width of one or more electrodes or other material of a sensor).

In addition to considerations regarding flexibility, it is often desirable that implantable sensors should have a substrate which is non-toxic. For example, the substrate may be approved by one or more appropriate governmental agencies or private groups for in vivo use.

Although the sensor substrate, in at least some embodiments, has uniform dimensions along the entire length of the sensor, in other embodiments, the substrate has a distal end or tail portion and a proximal end or body portion with different widths, respectively, as illustrated in FIG. 5A. In these embodiments, the distal end 530 of the sensor may have a relatively narrow width. For in vivo sensors which are implantable into the subcutaneous tissue or another portion of a patient's body, the narrow width of the distal end of the substrate may facilitate the implantation of the sensor. Often, the narrower the width of the sensor, the less pain the patient will feel during implantation of the sensor and afterwards.

For subcutaneously implantable sensors which are designed for continuous or semi-continuous monitoring of the analyte during normal activities of the patient, a tail portion or distal end of the sensor which is to be implanted into the patient may have a width of about 2 mm or less, e.g., about 1 mm or less, e.g., about 0.5 mm or less, e.g., about 0.25 mm or less, e.g., about 0.15 mm or less. However, wider or narrower sensors may be used. The proximal end of the sensor may have a width larger than the distal end to facilitate the connection between the electrode contacts and contacts on a control unit, or the width may be substantially the same as the distal portion.

The thickness of the substrate may be determined by the mechanical properties of the substrate material (e.g., the strength, modulus, and/or flexibility of the material), the desired use of the sensor including stresses on the substrate arising from that use, as well as the depth of any channels or indentations that may be formed in the substrate, as discussed below. The substrate of a subcutaneously implantable sensor for continuous or semi-continuous monitoring of the level of an analyte while the patient engages in normal activities may have a thickness that ranges from about 50 µm to about 500 µm, e.g., from about 100 µm to about 300 µm. However, thicker and thinner substrates may be used.

The length of the sensor may have a wide range of values depending on a variety of factors. Factors which influence the length of an implantable sensor may include the depth of implantation into the patient and the ability of the patient to manipulate a small flexible sensor and make connections between the sensor and the sensor control unit/transmitter. A subcutaneously implantable sensor of FIG. 5A may have an overall length ranging from about 0.3 to about 5 cm, however, longer or shorter sensors may be used. The length of the tail portion of the sensor (e.g., the portion which is subcutaneously inserted into the patient) is typically from about 0.25 to about 2 cm in length. However, longer and shorter portions may be used. All or only a part of this narrow portion may be subcutaneously implanted into the patient. The lengths of other implantable sensors will vary depending, at least in part, on the portion of the patient into which the sensor is to be implanted or inserted.

Electrodes 501, 502 and 503 are formed using conductive traces disposed on the substrate 504. These conductive traces may be formed over a smooth surface of the substrate or within channels formed by, for example, embossing, indenting or otherwise creating a depression in the substrate. The conductive traces may extend most of the distance along a length of the sensor, as illustrated in FIG. 5A, although this is not necessary. For implantable sensors, particularly subcutaneously implantable sensors, the conductive traces typically may extend close to the tip of the sensor to minimize the amount of the sensor that must be implanted.

The conductive traces may be formed on the substrate by a variety of techniques, including, for example, photolithography, screen printing, or other impact or non-impact printing techniques. The conductive traces may also be formed by carbonizing conductive traces in an organic (e.g., polymeric or plastic) substrate using a laser. A description of some exemplary methods for forming the sensor is provided in U.S. patents and applications noted herein, including U.S. Pat. Nos. 5,262,035, 6,103,033, 6,175,752 and 6,284,478, the disclosures of each of which are incorporated herein by reference for all purposes.

Another method for disposing the conductive traces on the substrate includes the formation of recessed channels in one or more surfaces of the substrate and the subsequent filling of these recessed channels with a conductive material. The recessed channels may be formed by indenting, embossing, or otherwise creating a depression in the surface of the substrate. Exemplary methods for forming channels and electrodes in a surface of a substrate can be found in U.S. Pat. No. 6,103,033, the disclosure of which is incorporated herein by reference for all purposes. The depth of the channels is typically related to the thickness of the substrate. In one embodiment, the channels have depths in the range of about 12.5 µm to about 75 µm, e.g., about 25 µm to about 50 µm.

The conductive traces are typically formed using a conductive material such as carbon (e.g., graphite), a conductive polymer, a metal or alloy (e.g., gold or gold alloy), or a metallic compound (e.g., ruthenium dioxide or titanium dioxide). The formation of films of carbon, conductive polymer, metal, alloy, or metallic compound are well-known and include, for example, chemical vapor deposition (CVD), physical vapor deposition, sputtering, reactive sputtering, printing, coating, and painting. In embodiments in which the conductive material is filled into channels formed in the substrate, the conductive material is often formed using a precursor material, such as a conductive ink or paste. In these embodiments, the conductive material is deposited on the substrate using methods such as coating, painting, or applying the material using a spreading instrument, such as a coating blade. Excess conductive material between the channels is then removed by, for example, running a blade along the substrate surface.

In certain embodiments, some or all of the electrodes 501, 502, 503 may be provided on the same side of the substrate 504 in the layered construction as described above, or alternatively, may be provided in a co-planar manner such that two or more electrodes may be positioned on the same plane (e.g., side-by side (e.g., parallel) or angled relative to each other) on the substrate 504. For example, co-planar electrodes may include a suitable spacing there between and/or include dielectric material or insulation material disposed between the conducting layers/electrodes. Furthermore, in certain embodiments, one or more of the electrodes 501, 502, 503 may be disposed on opposing sides of the substrate 504. Variations of such double-sided sensors are illustrated in FIGS. 6 and 7, discussed and described in detail below. In such double-sided sensor embodiments, the corresponding electrode contacts may be on the same or different sides of the substrate. For example, an electrode may be on a first side and its respective contact may be on a second side, e.g., a trace connecting the electrode and the contact may traverse through the substrate.

As noted above, analyte sensors include an analyte-responsive enzyme to provide a sensing component or sensing layer 508 proximate to or on a surface of a working electrode in order to electrooxidize or electroreduce the target analyte on the working electrode. Some analytes, such as oxygen, can be directly electrooxidized or electroreduced, while other analytes, such as glucose and lactate, require the presence of at least one component designed to facilitate the electrochemical oxidation or reduction of the analyte. The sensing layer may include, for example, a catalyst to catalyze a reaction of the analyte and produce a response at the working electrode, an electron transfer agent to transfer electrons between the analyte and the working electrode (or other component), or both.

In certain embodiments, the sensing layer includes one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes such as ferrocene. Examples of inorganic redox species are hexacyanoferrate (III), ruthenium hexamine etc.

In certain embodiments, electron transfer agents have structures or charges which prevent or substantially reduce the diffusional loss of the electron transfer agent during the period of time that the sample is being analyzed. For example, electron transfer agents include, but are not limited to, a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. It will be recognized that many redox species described for use with a polymeric component may also be used, without a polymeric component.

One type of polymeric electron transfer agent contains a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation. Another example of an ionically-bound mediator is a positively charged polymer such as quaternized poly(4-vinyl pyridine) or poly(l-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(l-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include, but are not limited to, 4,4'-dimethyl-2,2'-bipyridine and mono-, di-, and polyalkoxy-2,2'-bipyridines, such as 4,4'-dimethoxy-2,2'-bipyridine. Derivatives of 1,10-phenanthroline for complexation with the osmium cation include, but are not limited to, 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include, but are not limited to, polymers and copolymers of poly(l-vinyl imidazole) (referred to as "PVI") and poly(4-vinyl pyridine) (referred to as "PVP"). Suitable copolymer substituents of poly(l-vinyl imidazole) include acrylonitrile, acrylamide, and substituted or quaternized N-vinyl imidazole, e.g., electron transfer agents with osmium complexed to a polymer or copolymer of poly(l-vinyl imidazole).

Embodiments may employ electron transfer agents having a redox potential ranging from about −200 mV to about +200 mV versus the standard calomel electrode (SCE).

As mentioned above, the sensing layer may also include a catalyst which is capable of catalyzing a reaction of the analyte. The catalyst may also, in some embodiments, act as an electron transfer agent. When the analyte of interest is glucose, a catalyst such as a glucose oxidase, glucose dehydrogenase (e.g., pyrroloquinoline quinone (PQQ), dependent glucose dehydrogenase or oligosaccharide dehydrogenase, flavine adenine dinucleotide (FAD) dependent glucose dehydrogenase, or nicotinamide adenine dinucleotide (NAD) dependent glucose dehydrogenase) may be used. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

Certain embodiments include a Wired Enzyme™ sensing layer (such as used in the FreeStyle Navigator® continuous glucose monitoring system by Abbott Diabetes Care Inc.) that works at a gentle oxidizing potential, e.g., a potential of about +40 mV. This sensing layer uses an osmium (Os)-based mediator designed for low potential operation and is stably anchored in a polymeric layer. Accordingly, in certain embodiments the sensing element is redox active component that includes (1) Osmium-based mediator molecules attached by stable (bidente) ligands anchored to a polymeric backbone, and (2) glucose oxidase enzyme molecules. These two constituents are crosslinked together.

In certain embodiments, the sensing system detects hydrogen peroxide to infer glucose levels. For example, a hydrogen peroxide-detecting sensor may be constructed in which a sensing layer includes enzymes such as glucose oxidase, glucose dehydrogenase, or the like, and is positioned proximate to the working electrode. The sensing layer may be covered by one or more layers, e.g., a membrane that is selectively permeable to glucose. Once the glucose passes through the membrane, it may be oxidized by the enzyme and reduced glucose oxidase can then be oxidized by reacting with molecular oxygen to produce hydrogen peroxide.

Certain embodiments include a hydrogen peroxide-detecting sensor constructed from a sensing layer prepared by crosslinking two components together, for example: (1) a redox compound such as a redox polymer containing pendent Os polypyridyl complexes with oxidation potentials of about +200 mV vs. SCE, and (2) periodate oxidized horseradish peroxidase (HRP). Such a sensor functions in a reductive mode; the working electrode is controlled at a potential negative to that of the Os complex, resulting in mediated reduction of hydrogen peroxide through the HRP catalyst.

In another example, a potentiometric sensor can be constructed as follows. A glucose-sensing layer is constructed by crosslinking together (1) a redox polymer containing pendent Os polypyridyl complexes with oxidation potentials from about −200 mV to +200 mV vs. SCE, and (2) glucose oxidase. This sensor can then be used in a potentiometric mode, by exposing the sensor to a glucose containing solution, under conditions of zero current flow, and allowing the ratio of reduced/oxidized Os to reach an equilibrium value. The reduced/oxidized Os ratio varies in a reproducible way with the glucose concentration, and will cause the electrode's potential to vary in a similar way.

The components of the sensing layer may be in a fluid or gel that is proximate to or in contact with the working electrode. Alternatively, the components of the sensing layer may be disposed in a polymeric or sol-gel matrix that is proximate to or on the working electrode. Preferably, the components of the sensing layer are non-leachably disposed within the sensor. More preferably, the components of the sensor are immobilized within the sensor.

Examples of sensing layers that may be employed are described in U.S. patents and applications noted herein, including, e.g., in U.S. Pat. Nos. 5,262,035, 5,264,104, 5,543,326, 6,605,200, 6,605,201, 6,676,819 and 7,299,082, the disclosures of each of which are incorporated herein by reference for all purposes.

Regardless of the particular components that make up a given sensing layer, a variety of different sensing layer configurations may be used. In certain embodiments, the sensing layer covers the entire working electrode surface, e.g., the entire width of the working electrode surface. In other embodiments, only a portion of the working electrode surface is covered by the sensing layer, e.g., only a portion of the width of the working electrode surface. Alternatively, the sensing layer may extend beyond the conductive material of the working electrode. In some cases, the sensing layer may also extend over other electrodes, e.g., over the counter electrode and/or reference electrode (or counter/reference is provided), and may cover all or only a portion thereof.

In other embodiments the sensing layer is not deposited directly on the working electrode. Instead, the sensing layer may be spaced apart from the working electrode, and separated from the working electrode, e.g., by a separation layer. A separation layer may include one or more membranes or films or a physical distance. In addition to separating the working electrode from the sensing layer the separation layer may also act as a mass transport limiting layer, and/or an interferent eliminating layer, and/or a biocompatible layer.

In certain embodiments which include more than one working electrode, one or more of the working electrodes may not have a corresponding sensing layer, or may have a sensing layer which does not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing layers by, for example, subtracting the signal.

Whichever configuration of the sensing component or layer is employed, at least one factor in minimizing variations in sensor sensitivity, at least within the same sensor batch or lot (or all sensors made according to the same specification), is by strictly maintaining the dimensions (width, length, diameter and thickness) of the active area, i.e., the area of the working electrode in contact with the sensing component or layer, from sensor to sensor. Optimizing sensitivity, including reproducing substantially the same sensitivity for sensors within a lot or batch of sensors, reduces and in certain embodiments eliminates the need for sensor calibration, by the user. Accordingly, sensors that do not require a user to calibrate, using for example an in vitro test strip or the like after insertion of the sensor into the body for testing, are achieved. Examples of sensors for use in one or more embodiments of the present disclosure can be found in, among others, U.S. patent application Ser. No. 12/714,439, the disclosure of which is incorporated herein by reference for all purposes.

Calibration, when an electrochemical glucose sensor is used, generally involves converting the raw current signal (nA) into a glucose concentration (mg/dL). One way in which this conversion is done is by relating or equating the raw analyte signal with a calibration measurement (i.e., with a reference measurement), and obtaining a conversion factor (raw analyte signal/reference measurement value). This relationship is often referred to as the sensitivity of the sensor, which, once determined, may then be used to convert sensor signals to calibrated analyte concentration values, e.g., via simple division (raw analyte signal/sensitivity=calibrated analyte concentration). For example, a raw analyte signal of 10 nA could be associated with a calibration analyte concentration of 100 mg/dL, and thus, a subsequent raw analyte signal of 20 nA could be converted to an analyte concentration of 200 mg/dL, as may be appropriate for a given analyte, such as glucose, for example.

There are many ways in which the conversion factor may be obtained. For example, the sensitivity factor can be derived from a simple average of multiple analyte signal/calibration measurement data pairs, or from a weighted average of multiple analyte signal/calibration measurement data pairs. Further by way of example, the sensitivity may be modified based on an empirically derived weighting factor, or the sensitivity may be modified based on the value of another measurement, such as temperature. It will be appreciated that any combination of such approaches, and/or other suitable approaches, is contemplated herein.

For subcutaneous glucose sensors, calibration at the site of manufacture, that may be relied upon to calibrate sensor signal for the useful life of a sensor, presents numerous challenges to the feasibility. This infeasibility may be based on any of a number of factors. For example, variations in the within-lot sensitivity of the analyte sensors and/or variations in sensor drift may be too great.

The present disclosure provides sensor embodiments which attempt to address both the in vivo environmental effects and the manufacturing-based inconsistencies which can lead to variation in sensor sensitivity, and/or which obviate the need for any form of calibration, whether at the factory or by the user, at anytime prior to or during operative use of the sensor.

Certain of these sensor embodiments are double-sided, i.e., both sides of the sensor's substrate are electrochemically functional, with each side providing at least one electrode. Because both sides of the sensor are utilized, the smaller the necessary surface area required per side to host the electrodes. This space-efficient construct allows the sensor to be miniaturized and much smaller than conventional sensors, and, in particular, have a relatively narrower tail portion, i.e., at least the portion of a sensor that is constructed to be positioned beneath a skin surface of a user is miniaturized. A narrower structure reduces trauma to tissue at the implantation site, thereby reducing bleeding and the production of thrombi around the sensor. The smaller structure also minimizes impingement upon adjacent blood vessels. The smaller width of the sensor allows, in addition to perpendicular diffusion of the analyte (e.g., glucose), for the lateral diffusion of analyte molecules towards the active sensing area. These effects substantially if not completely eliminate spurious low readings.

In addition to providing micro tail sections, these double-sided sensors are designed and configured to be highly reproducible. Further, they may be fabricated by methods, techniques and equipment which minimize inconsistencies in the registration, deposition and resolution of the sensor components, as described herein.

Figure 6A:
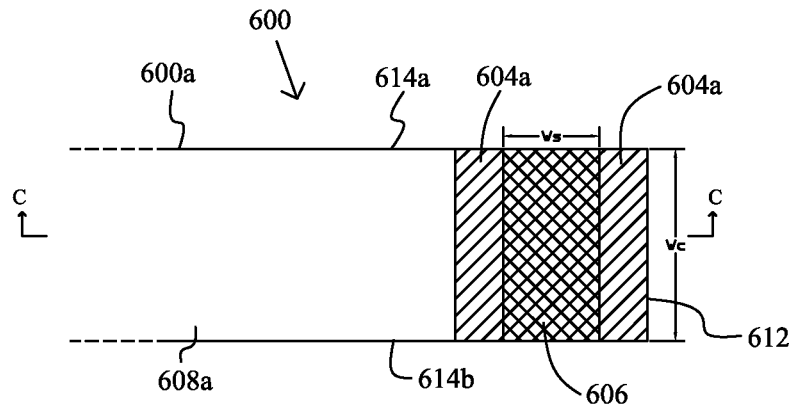
FIGS. 6A, 6B and 6C show top, bottom and cross-sectional side views, respectively, of an embodiment of a two-sided analyte sensor usable with the present disclosure.
Figure 6B:
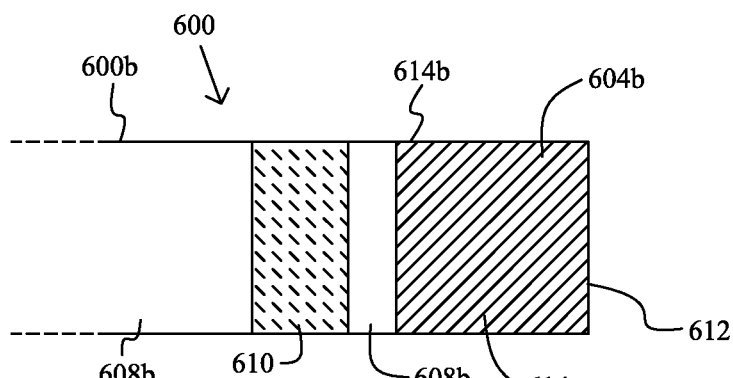
Figure 6C:
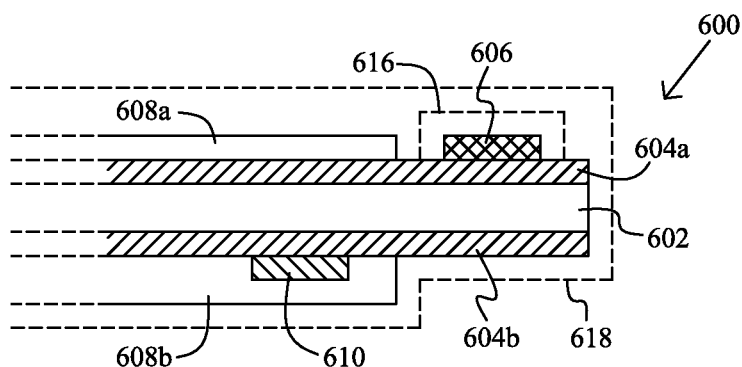

Referring now to FIGS. 6A-6C, an example of such a double-sided sensor in which an implantable portion of the sensor 600, e.g., the distal portion of the sensor's tail section, is illustrated. In particular, FIGS. 6A and 6B provide top and bottom views, respectively, of tail section 600 and FIG. 6C provides a cross-sectional side view of the same taken along lines C-C in FIG. 6A.

Sensor tail portion 600 includes a substrate 602 (see FIG. 6C) having a top conductive layer 604a which substantially covers the entirety of the top surface area of substrate 602, i.e., the conductive layer substantially extends the entire length of the substrate to distal edge 612 and across the entire width of the substrate from side edge 614a to side edge 614b. Similarly, the bottom conductive layer 604b substantially covers the entirety of the bottom side of the substrate of tail portion 600. However, one or both of the conductive layers may terminate proximally of distal edge 612 and/or may have a width which is less than that of substrate 602 where the width ends a selected distance from the side edges 614a, 614b of the substrate, which distance may be equidistant or vary from each of the side edges.

One of the top or bottom conductive layers, here, top conductive layer 604a, serves as the sensor's working electrode. The opposing conductive layer, here, bottom conductive layer 604b, serves as a reference and/or counter electrode. Where conductive layer 604b serves as either a reference or counter electrode, but not both, a third electrode may optionally be provided on a surface area of the proximal portion of the sensor (not shown). For example, conductive layer 604b may serve as reference electrode and a third conductive trace (not shown), present only on the non-implantable proximal portion of the sensor, may serve as the sensor's counter electrode.

Disposed over a distal portion of the length of conducting layer/working electrode 604a is sensing component or layer 606. Providing the sensing layer closer to the distal tip of the sensor places the sensing material in the best position for contact with the analyte-containing fluid. As only a small amount of sensing material is required to facilitate electrooxidization or electroreduction of the analyte, positioning the sensing layer 606 at or near the distal tip of the sensor tail reduces the amount of material needed. Sensing layer 606 may be provided in a continuous stripe/band between and substantially orthogonal to the substrate's side edges 614a, 614b with the overlap or intersection of working electrode 604a and the sensing layer 606 defining the sensor's active area. Due to the orthogonal relationship between sensing layer 606 and conductive layer 604a, the active area has a rectilinear polygon configuration; however, any suitable shape may be provided. The dimensions of the active area may be varied by varying either or both of the respective width dimensions of the sensing and conducting layers. The width $W_S$ of the sensing layer 606 may cover the entire length of the working electrode or only a portion thereof. As the width $W_C$ of the conductive layer is dictated by the width of the tail portion's substrate in this embodiment, any registration or resolution inconsistencies between the conductive layer and the substrate are obviated. In certain embodiments, the width of the sensing layer $W_S$ is in the range from about 0.05 mm to about 5 mm, e.g., from about 0.1 mm to about 3 mm; the width of the conductive layer $W_C$ is in the range from about 0.05 mm to about 0.6 mm, e.g., from about 0.1 mm to about 0.3 mm, with the resulting active area in the range from about 0.0025 mm$^2$ to about 3 mm$^2$, e.g., from about 0.01 mm$^2$ to about 0.9 mm$^2$.

Referring again to the electrodes, the same materials and methods may be used to make the top and bottom electrodes, although different materials and methods may also be used. With the working and reference electrodes positioned on opposing sides of the substrate as in the illustrated embodiment of FIGS. 6A-6C, it is not additionally inconvenient to use two or more different types of conductive material to form the respective electrodes as only one type of conductive material would need to be applied to each side of the substrate, thereby reducing the number of steps in the manufacturing process.

Selection of the conductive materials for the respective electrodes is based in part on the desired rate of reaction of the sensing layer's mediator at an electrode. In some instances the rate of reaction for the redox mediator at the counter/reference electrode is controlled by, for example, choosing a material for the counter/reference electrode that would require an overpotential or a potential higher than the applied potential to increase the reaction rate at the counter/reference electrode. For example, some redox mediators may react faster at a carbon electrode than at a silver/silver chloride (Ag/AgCl) or gold electrode. However, as Ag/AgCl and gold are more expensive than carbon, it may be desirous to use the former materials judiciously.

Figure 7A:
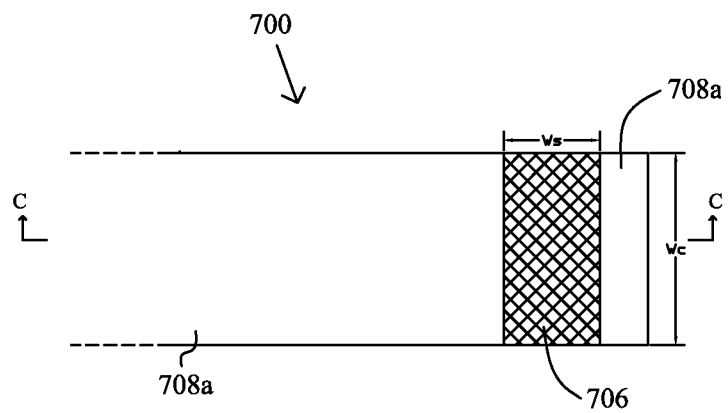
FIGS. 7A, 7B and 7C show top, bottom and cross-sectional side views, respectively, of another embodiment of a two-sided analyte sensor usable with the present disclosure.
Figure 7B:
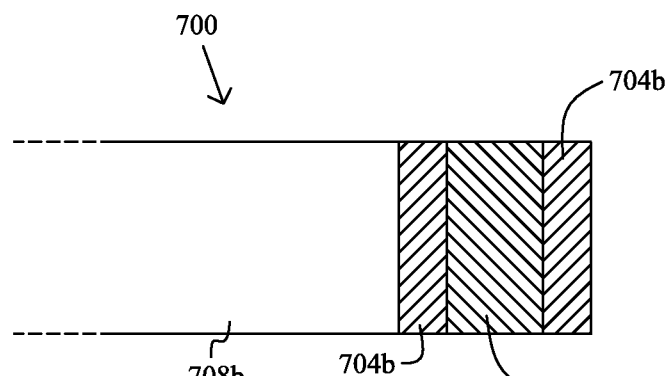
Figure 7C:
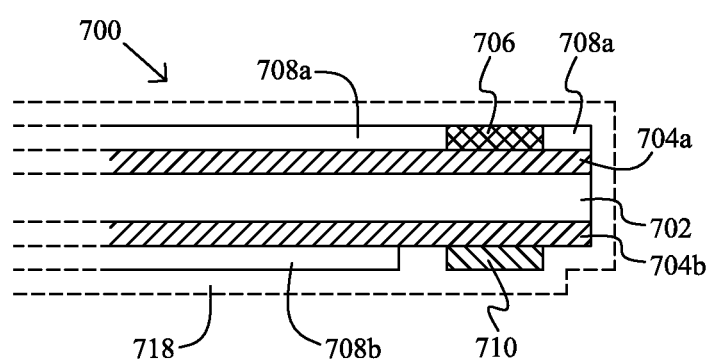

The sensor embodiment of FIGS. 6A-6C provides such a construct in which the full-length conductive layers 604a, 604b may be of a material such as carbon with a secondary layer of conductive layer 610 of a material such as Ag/AgCl disposed over a distal portion of bottom conductive layer 604b to collectively form the sensor's reference electrode. As with sensing layer 606, conductive material 610 may be provided in a continuous stripe/band between and substantially orthogonal to the substrate's side edges 614a, 614b. While layer 610 is shown positioned on substrate 602 proximally of sensing layer 606 (but on the opposite side of the substrate), layer 610 may be positioned at any suitable location on the tail portion 600 of the reference electrode 604b. For example, as illustrated in FIGS. 7A-7C, the secondary conductive material 710 of reference electrode 708b may be aligned with and/or distal to sensing layer 706 with dimensions $W_S$ and $W_C$.

Referring again to sensor 600, an insulation/dielectric layer 608a, 608b is disposed on each side 600a, 600b of the sensor, over at least the sensor's body portion (not shown), to insulate the proximal portion of the electrodes, i.e., the portion of the electrodes which in part remains external to the skin upon implantation. The top dielectric layer 608a disposed on the working electrode 604a may extend distally to but preferably not over any portion of sensing layer 606. Alternatively, as illustrated in FIGS. 7A-7C, dielectric layer 708a on the working electrode side of the sensor 700 may be provided prior to sensing layer 706 whereby the dielectric layer 708a has at least two portions spaced apart from each other on conductive layer 704a, best illustrated in FIG. 7C. FIG. 7C provides a cross-sectional side view taken along lines C-C in FIG. 7A. The sensing material 706 is then provided in the spacing between the two portions.

As for the dielectric layer on the bottom/reference electrode side of the sensor, it may extend any suitable length of the sensor's tail section, i.e., it may extend the entire length of both of the primary and secondary conductive layers or portions thereof. For example, as illustrated in FIGS. 6A-6C, bottom dielectric layer 608b extends over the entire bottom surface area of secondary conductive material 610 but terminates proximally of the distal edge 612 of the length of the primary conductive layer 604b. It is noted that at least the ends of the secondary conductive material 610 which extend along the side edges 614a, 614b of the substrate 602 are not covered by dielectric layer 608b and, as such, are exposed to the in vivo environment when in operative use. In contrast, as illustrated in FIGS. 7A-7C, bottom dielectric layer 708b has a length which terminates proximally of secondary conductive layer 710 on bottom primary conductive layer 704b along substrate 702. Additional conducting and dielectric layers may be provided on either or both sides of the sensors, as described above.

Finally, one or more membranes, which may function as one or more of an analyte flux modulating layer and/or an interferent-eliminating layer and/or biocompatible layer, discussed in greater detail below, may be provided about the sensor, e.g., as one or more of the outermost layer(s). In certain embodiments, as illustrated in FIG. 6C, a first membrane layer 616 may be provided solely over the sensing component or sensing layer 606 on the working electrode 604*a* to modulate the rate of diffusion or flux of the analyte to the sensing layer. For embodiments in which a membrane layer is provided over a single component/material, it may be suitable to do so with the same striping configuration and method as used for the other materials/components. Here, the stripe/band of membrane material 616 preferably has a width greater than that of sensing stripe/band 606. As it acts to limit the flux of the analyte to the sensor's active area, and thus contributes to the sensitivity of the sensor, controlling the thickness of membrane 616 is important. Providing membrane 616 in the form of a stripe/band facilitates control of its thickness. A second membrane layer 618, which coats the remaining surface area of the sensor tail, may also be provided to serve as a biocompatible conformal coating and provide smooth edges over the entirety of the sensor. In other sensor embodiments, as illustrated in FIG. 7C, a single, homogenous membrane 718 may be coated over the entire sensor surface area, or at least over both sides of the distal tail portion. It is noted that to coat the distal and side edges of the sensor, the membrane material would have to be applied subsequent to singulation of the sensor precursors.

Based on current sensor fabrication techniques, provision of the sensor's conductive layers can be accomplished more accurately than provision of the sensing layers. As such, improving upon the accuracy of providing the sensing component on the sensor, and thus, the accuracy of the resulting active area, may significantly decrease any sensor to sensor sensitivity variability and obviate the need for calibration of the sensor. Accordingly, the present disclosure also includes methods for fabricating such analyte sensors having accurately defined active areas. Additionally, the methods provide finished sensors which are smaller than currently available sensors with micro-dimensioned tail portions which are far less susceptible to the in situ environmental conditions which can cause spurious low readings.

In one variation of the subject methods, web-based manufacturing techniques are used to perform one or more steps in fabricating the subject sensors, many of the steps of which are disclosed in U.S. Pat. No. 6,103,033. To initiate the fabrication process, a continuous film or web of substrate material is provided and heat treated as necessary. The web may have precuts or perforations defining the individual sensor precursors. The various conductive layers are then formed on the substrate web by one or more of a variety of techniques as described above, with the working and reference (or counter/reference) electrode traces provided on opposite sides of the web. As mentioned previously, the electrode traces may be provided in channels formed in the surface of the substrate material; however, with the desire to provide a sensor having a tail portion that has the smallest functional profile possible, and particularly with the sensor tail having two functional sides, the use of channels may not be optimal as it requires a thicker substrate material. Also, as mentioned previously, a third, optional electrode trace (which may function as a counter electrode, for example) may be provided on the proximal body portion of the sensor precursors. The "primary" conductive traces provided on the area of the tail portions of the precursor sensors have a width dimension greater than the intended width dimension of the tail portions of the finalized sensors. The precursor widths of these conductive traces may range from about 0.3 mm to about 10 mm including widths in range from about 0.5 mm to about 3 mm, or may be even narrower. The primary conductive layers are formed extending distally along the tail section of the sensor precursors to any suitable length, but preferably extend at least to the intended distal edge of the finalized sensors to minimize the necessary sensor tail length.

Next, the sensing layer and secondary conductive layers, if employed, are formed on the primary conductive layers on the respective sides of the substrates or substrate web. As discussed, each of these layers is preferably formed in a stripe or band of the respective material disposed orthogonally to the length of the primary conductive layer/sensor tail. With a single, continuous deposition process, the mean width of the sensing strip is substantially constant along the substrate webbing, and ultimately, from sensor to sensor. The secondary conductive layer (e.g., Ag/AgCl on the reference electrode), if provided, may also be formed in a continuous orthogonal stripe/band with similar techniques. One particular method of providing the various stripes/band of material on the sensors is by depositing, printing or coating the sensing component/material by means of an inkjet printing process (e.g., piezoelectric inkjet as manufactured by Scienion Inc. and distributed by BioDot Inc.). Another way of applying these materials is by means of a high precision pump (e.g., those which are piston driven or driven by peristaltic motion) and/or footed needle. The respective stripes/bands may be provided over a webbing of sequentially aligned sensor precursors prior to singulation of the sensors or over a plurality of sensors/electrodes where the sensors have been singulated from each other prior to provision of the one or more stripes/bands.

With both the sensing and conductive layers/strips having substantially constant widths and provided substantially orthogonal to each other, the active area which their intersection forms is also substantially constant along both the length and width of the sensor. In such embodiments, the active area (as well as the intersecting area of the primary and secondary conductive layers which form the reference electrode) has a rectilinear polygonal shape which may be easier to provide in a reproducible manner from sensor to sensor; however, any relative arrangement of the layers resulting in any suitable active area geometry may be employed.

The sensor precursors, i.e., the template of substrate material (as well as the conductive and sensing materials if provided on the substrate at the time of singulation), may be singulated from each other using any convenient cutting or separation protocol, including slitting, shearing, punching, laser singulation, etc. These cutting methods are also very precise, further ensuring that the sensor's active area, when dependent in part on the width of the sensor (i.e., the tail portion of the substrate), has very accurate dimensions from sensor to sensor. Moreover, with each of the materials (i.e., the primary and secondary conductive materials, sensing component, dielectric material, membrane, etc.) provided with width and/or length dimensions extending beyond the intended dimensions or boundaries of the final sensors, issues with resolution and registration of the materials is minimized if not obviated altogether.

The final, singulated, double-sided sensor structures have dimensions in the following ranges: widths from about 500 μm to about 100 including widths in range from about 300 μm to about 150 μm; tail lengths from about 10 mm to about 3 mm, including lengths in range from about 6 mm to about 4 mm; and thicknesses from about 500 μm to about 100 including thicknesses in range from about 300 μm to about 150 μm. As such, the implantable portions of the sensors are reduced in size from conventional sensors by approximately 20% to about 80% in width as well as in cross-section. The reduced size minimizes bleeding and thrombus formation upon implantation of the sensor and impingement on adjacent tissue and vessels, thereby minimizing impediment to lateral diffusion of the analyte to the sensor's sensing component or sensing layer.

The substrate web may have precuts or perforations that provide guidance for the final cut employed to singulate the precursors. Depending on the layout and orientation of the sensor precursors, the singulation lines may be at fixed or varying intervals. For example, if the orientation and spacing of the sensor precursors are serial and constant over the area of the substrate material, the singulation lines will typically be at fixed intervals in all directions. However, where the sensors having irregular or asymmetrical shapes (e.g., as illustrated in FIG. 5A) it may be preferential to orient the sensor precursors in an alternating (e.g., head to toe) or in mirroring (e.g., back to back) arrangements to minimize the unused substrate material and any of the sensor materials deposited thereon. Where the orientation of the sensor precursors is alternating or in a mirroring arrangement, the singulation lines may not be at fixed intervals.

Embodiments include sensor lots having very low variations in sensitivity of sensors within the lot. Low sensitivity variation enables sensors that do not require calibration by a user after a sensor is positioned in the body. Accordingly, in certain embodiments, sensor lots are provided that have a coefficient of variation (CV) of about 5% or less, e.g., about 4.5% or less, e.g., about 4% or less, e.g., about 3% or less.

Sensors having predictable sensor in vivo sensitivity and signal are provided. For example, sensors having predictable shelf life sensitivity drift (the period of time between manufacture and use) and predictable in vivo sensitivity drift, including substantially no shelf and in vivo sensitivity drift, are also provided. In embodiments in which sensors have drift (e.g., where the sensor sensitivity drifts an expected percentage over a certain time), a drift profile is contemplated. This drift profile may be contemplated by an algorithm of the monitoring system to determine a drift correction factor that may be applied to sensor signal to obtain a glucose measurement (mg/dL). Due, at least in part, to the high reproducibility of the manufacturing process that results in low manufacturing coefficient of variation (CV), a single drift correction factor may be used for all sensors of a given sensor manufacturing lot or batch.

In certain embodiments, sensor sensitivity may be determined post-fabrication by the manufacturer at the site of manufacture. This "factory-determined" sensitivity may then be used in an algorithm to calibrate sensor signal for the useable lifetime of the sensor, negating the need for a user to obtain a reference value, e.g., from a test strip, for calibration. Sensitivity may include determining the relationship of sensor signal to a reference such as an in vitro reference (a known glucose level to which one or more sensors of a sensor lot may be compared). Sensitivity may include determining a conversion factor as described herein. In certain embodiments, the determined sensitivity may be further augmented. For example, one or more additional factors (e.g., to account for the relationship of blood to subcutaneous tissue glucose, effect of oxygen, temperature, etc.) may be contemplated. In any event, a sensitivity value is determined. Exemplary calibration protocols are described, e.g., in U.S. Pat. No. 7,299,082, the disclosure of which is incorporated herein by reference for all purposes.

Because the sensitivities of each sensor of a given manufacturing lot are substantially the same according to the embodiments herein, the factory-determined sensitivity may be applied to all sensors of such a lot, i.e., a single calibration algorithm may be used for all the sensors of a given lot. In one embodiment, the information is programmed or is programmable into software of the monitoring system, e.g., into one or more processors. For example, the factory-determined sensitivity may be provided to a user with a sensor(s) and uploaded to a calibration algorithm manually or automatically (e.g., via bar code and reader, or the like). Calibration of sensor signal may then be implemented using suitable hardware/software of the system.

A mass transport limiting layer or membrane, e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations. Mass transport limiting layers may include polymers and may be biocompatible. A mass transport limiting layer may provide many functions, e.g., biocompatibility and/or interferent-eliminating, etc.

A membrane may be formed by crosslinking in situ a polymer, modified with a zwitterionic moiety and a non-pyridine copolymer component. The modified polymer may be made from a precursor polymer containing heterocyclic nitrogen groups. For example, a precursor polymer may be polyvinylpyridine or polyvinylimidazole. Embodiments also include membranes that are made of a polyurethane, or polyether urethane, or chemically related material, or membranes that are made of silicone, and the like.

Optionally, another moiety or modifier that is either hydrophilic or hydrophobic, and/or has other desirable properties, may be used to "fine-tune" the permeability of the resulting membrane to an analyte of interest. Optional hydrophilic modifiers, such as poly(ethylene glycol), hydroxyl or polyhydroxyl modifiers, may be used to enhance the biocompatibility of the polymer or the resulting membrane.

The membrane may also be formed in situ by applying an alcohol-buffer solution of a crosslinker and a modified polymer over an enzyme-containing sensing layer and allowing the solution to cure for about one to two days or other appropriate time period. The crosslinker-polymer solution may be applied to the sensing layer by placing a droplet or droplets of the solution on the sensor, by dipping the sensor into the solution, or the like. Generally, the thickness of the membrane is controlled by the concentration of the solution, by the number of droplets of the solution applied, by the number of times the sensor is dipped in the solution, or by any combination of these factors. A membrane applied in this manner may have any combination of the following functions: (1) mass transport limitation, i.e., reduction of the flux of analyte that can reach the sensing layer, (2) biocompatibility enhancement, or (3) interferent reduction. Exemplary mass transport layers are described in U.S. patents and applications noted herein, including, e.g., in U.S. Pat. Nos. 5,593,852, 6,881,551 and 6,932,894, the disclosures of each of which are incorporated herein by reference for all purposes.

A sensor may also include an active agent such as an anticlotting and/or antiglycolytic agent(s) disposed on at least a portion a sensor that is positioned in a user. An anticlotting agent may reduce or eliminate the clotting of blood or other body fluid around the sensor, particularly after insertion of the sensor. Examples of useful anticlotting agents include heparin and tissue plasminogen activator (TPA), as well as other known anticlotting agents. Embodiments may include an antiglycolytic agent or precursor thereof. Examples of antiglycolytic agents are glyceraldehyde, fluoride ion, and mannose.

The electrochemical sensors of the present disclosure may employ any suitable measurement technique, e.g., may detect current, may employ potentiometry, etc. Techniques may include, but are not limited to, amperometry, coulometry, and voltammetry. In some embodiments, sensing systems may be optical, colorimetric, and the like.

The subject analyte measurement systems may include an optional alarm system that, e.g., based on information from a processor, warns the patient of a potentially detrimental condition of the analyte. For example, if glucose is the analyte, an alarm system may warn a user of conditions such as hypoglycemia and/or hyperglycemia and/or impending hypoglycemia, and/or impending hyperglycemia. An alarm system may be triggered when analyte levels approach, reach or exceed a threshold value. An alarm system may also, or alternatively, be activated when the rate of change, or acceleration of the rate of change, in analyte level increase or decrease approaches, reaches or exceeds a threshold rate or acceleration. A system may also include system alarms that notify a user of system information such as battery condition, calibration, sensor dislodgment, sensor malfunction, etc. Alarms may be, for example, auditory and/or visual. Other sensory-stimulating alarm systems may be used including alarm systems which heat, cool, vibrate, or produce a mild electrical shock when activated.

The subject disclosure also includes sensors used in sensor-based drug delivery systems. The system may provide a drug to counteract the high or low level of the analyte in response to the signals from one or more sensors. Alternatively, the system may monitor the drug concentration to ensure that the drug remains within a desired therapeutic range. The drug delivery system may include one or more (e.g., two or more) sensors, a processing unit such as a transmitter, a receiver/display unit, and a drug administration system. In some cases, some or all components may be integrated in a single unit. A sensor-based drug delivery system may use data from the one or more sensors to provide necessary input for a control algorithm/mechanism to adjust the administration of drugs, e.g., automatically or semi-automatically. As an example, a glucose sensor may be used to control and adjust the administration of insulin from an external or implanted insulin pump.

Referring now to FIGS. 8A-12B, the continuous analyte measurement systems illustrated therein are particularly suitable for use with the double-sided analyte sensors disclosed herein. These systems include a skin-mounted portion or assembly and a remote portion or assembly. The skin-mounted portion includes at least the data transmitter, the transmitter battery and electrical contacts for electrically coupling the implanted sensor with the transmitter, and has a housing or base which is constructed to externally mount to the patient's skin and to mechanically and electrically couple the implanted sensor with the transmitter. Removably held or positioned within the housing/base structure is a connector piece having an electrical contact configuration which, when used with a double-sided sensor, enables coupling of the sensor to the transmitter in a low-profile, space-efficient manner. The remote portion of the system includes at least a data receiver and a user interface which may also be configured for test strip-based glucose monitoring. Various embodiments of these systems and methods of using them are now described in greater detail.

Figure 8A:
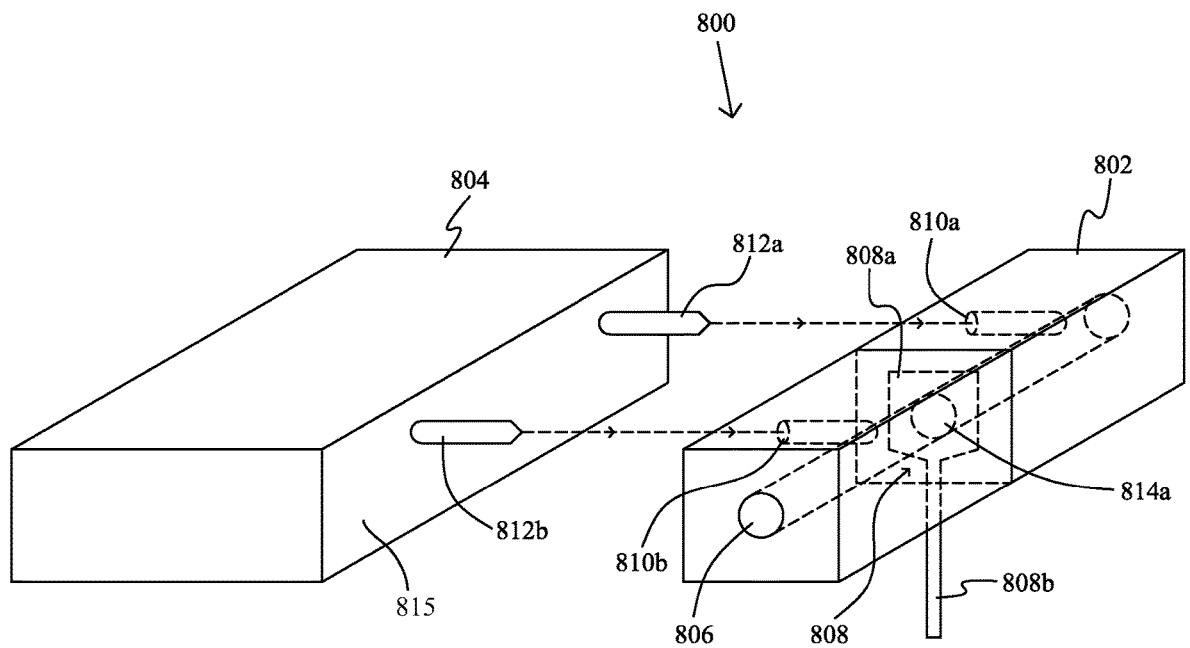
FIGS. 8A and 8B show perspective and top views, respectively, of one embodiment of a continuous analyte monitoring system of the present disclosure utilizing a double-sided analyte sensor.
Figure 8B:
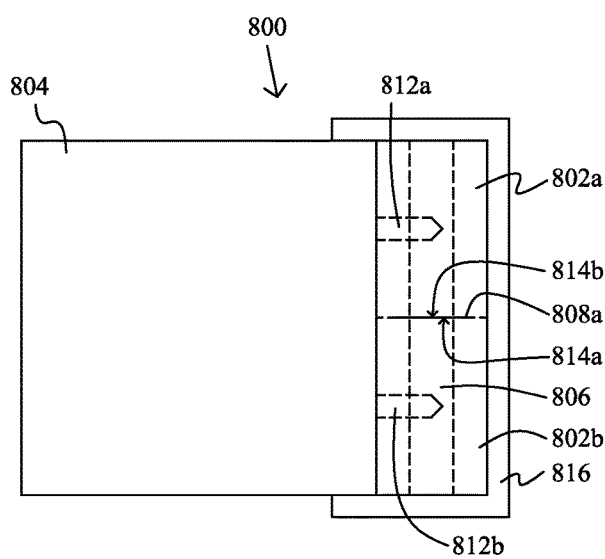

FIGS. 8A and 8B illustrate one embodiment of the skin-mounted portion or assembly 800 of a continuous analyte monitoring system of the present disclosure. Assembly 800 includes a connector or base 802 and a transmitter 804 both having rectangular or square constructs which, when operatively coupled together, are mounted side-by-side in the same plane on the skin. The underside of both components has an adhesive layer for securing to the skin surface. Connector 802 encases a conductive core or elongated member 806 extending along its length. Conductive core 806 is shown having a cylindrical configuration but may have any suitable shape. The connector body and conductive core may be made of any suitable non-conductive and conductive materials, respectively. To provide a non-rigid or semi-flexible embodiment, connector body 802 or the portion of it about the conductive core 806 may be made of a flexible or compressible material such as silicone, etc., and connector core 806 may be made of a conductive polymeric material, e.g., carbon-doped silicone. The connector 802 and its connector core 806 may be provided in two parts or halves 802a and 802b, whereby the system's analyte sensor 808, here, having two functional sides 808a and 808b, may be sandwiched therebetween. Each of the inner ends of core 806 abuts a respective electrode 814a, 814b of sensor 808. A bracket or fixture 816 may be employed to clamp together or apply pressure on opposing ends of the two connector body 802/connector core 806 pieces to ensure a sufficient, continuous electrical contact between connector core 806 and sensor electrodes 814a, 814b. The body of the connector 802 has hollowed holes or receptacles 810a, 810b within a side thereof which extend to or within conductive core 806. Holes 810a, 810b are dimensioned and spaced for receiving corresponding conductive pins 812a, 812b extending from an end 815 of transmitter 804. When the connector 802 and transmitter 804 are operatively coupled, as illustrated in FIG. 8B, pins 812a, 812b extend within and are in electrical communication with conductive core 806, and thus, with sensor 808. The compressible, non-conductive material of connector 802 provides a substantially hermetic seal between transmitter 804 and sensor 808. The transmitter housing may house a battery (not shown) for powering the transmitter 804, the sensor 808, and at least a portion of the system's control electronics, e.g., the data processing unit, etc.

Figure 9A:
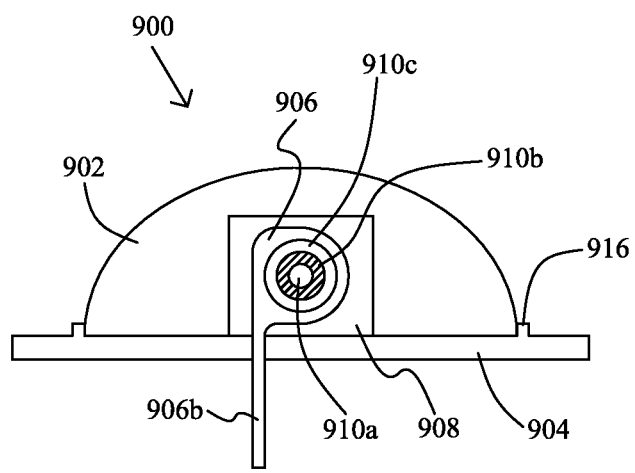
Figure 9B:
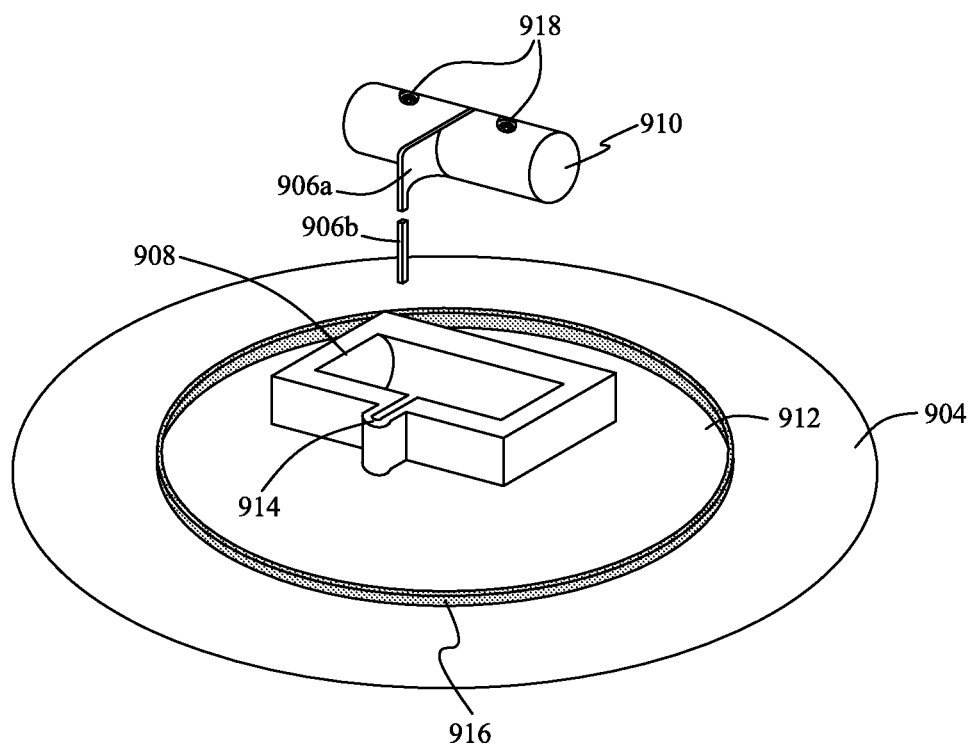

FIGS. 9A-9E illustrate another embodiment of the skin-mounted portion or assembly 900 of a continuous analyte monitoring system of the present disclosure. With reference to FIG. 9A, assembly 900 includes a transmitter 902 mounted atop a mounting structure or base 904, the underside of which has an adhesive layer for securing to the skin surface. Here, transmitter 902 has a round foot print and a convex, low-profile top surface. The transmitter housing may house a battery (not shown) for powering the transmitter 902, the sensor 906, and at least a portion of the system's control electronics, e.g., the data processing unit, etc. A raised rim 916 or similar feature on the top surface 912 of base 904 is shaped and dimensioned to securely hold transmitter 902 in a snap-fit configuration. Base 904 also has a centrally disposed cradle 908 on its top surface 912 for receiving and snugly holding a connector 910. As best shown in FIG. 9B, a sidewall of the base 904 has an outwardly extending portion 914 which defines a slit or keyhole therein to receive a sensor 906 (as well as an insertion needle, as will be explained below) when operatively held by connector 910. An aperture (not shown) within the bottom of cradle 908 allows passage of sensor tail 906b upon placement of connector 910 within the cradle 908. Cradle 908 may be sized to compress the ends of the connector 910 toward each other so as to ensure a constant electrical connection between the connector 910 and sensor 906.

As illustrated in FIGS. 9C-9E, connector 910 has a cylindrical configuration having several concentric layers or materials: a non-conductive inner member 910a, a conductive intermediate layer 910b, and an outer dielectric cover or shell 910c. In one embodiment, the cylindrical connector is compliant, with each of its layers made of compliant material(s) as described with respect to the embodiment of FIGS. 8A and 8B. The optional inner member 910a is made of a non-conductive compliant or substantially rigid material which extends through a hole 906c at the proximal end 906a of sensor 906 and, thus, acts as an alignment pin. The terminal ends of the working and reference electrodes of double-sided sensor 906 form a conductive area or ring 906d about hole 906c. Conductive ring 906d may be made of gold or another highly conductive material. The connector's intermediate layer 910b is made of a compliant conductive material, such as a conductive polymeric material as described with respect to the embodiment of FIGS. 8A and 8B, which abuts against both sides of conductive area 906d of the sensor. The outer shell 910c of the connector, which extends over and insulates each of the conductive ends of the intermediate layer 910b, is made of a compliant dielectric material, such as silicone, which ensures that the interconnection between the transmitter, connector and sensor is hermetically sealed. On a top surface of outer shell 910c are a pair of bores or holes 918 for receiving a corresponding pair of pins or plugs 920 extending from the bottom side of transmitter 902. The bores and pins may have respective mating configurations to ensure a snug fit and hermetically seal between transmitter 902 and connector 910. For example, as illustrated in FIG. 9E, bores 918 may have a stepped configuration and pins 920 may have a conical configuration. At least the distal tip 922 of each pin 920 is made of a conductive material, such as gold, to establish electrical communication between transmitter 902 and sensor 906.

FIGS. 10A-10F illustrate various steps in a method of the present disclosure for mounting the continuous analyte monitoring system's on-skin assembly 900, including implanting sensor 906 within the skin, utilizing an insertion device 1000 of the present disclosure. However, the sensor/connector may be configured to be manually inserted/mounted without the use of an insertion device.

Insertion device 1000 comprises a body 1002 having a distal base portion 1008 having a bottom surface configured for placement on the skin surface 1005. It is noted that the figures show, with solid drawing lines, components of the insertion device and the analyte monitoring system that would otherwise not be visible when positioned or housed within device body 1002 for purposes of illustration and ease of description. For example, in FIGS. 10A-10C, mounting base 904 of assembly 900 (FIG. 9A) is shown releasably held within an opening in the bottom surface of device body 1002. Insertion device 1000 further includes a plunger mechanism 1004 positioned within the housing 1002 and movable in a direction perpendicular to the skin surface 1005. The distal end of the plunger mechanism 1004 carries an insertion needle 1006. The components of insertion device 1000 are typically formed using structurally rigid materials, such as metal or rigid plastic. Preferred materials include stainless steel and ABS (acrylonitrile-butadiene-styrene) plastic.

Figure 11A:
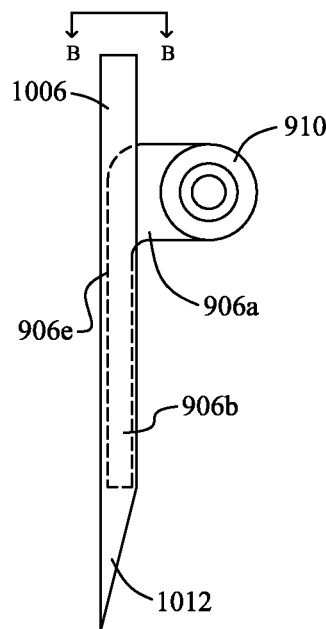
FIGS. 11A and 11B show side and top views, respectively, of an insertion needle of the insertion system of FIGS.
Figure 11B:
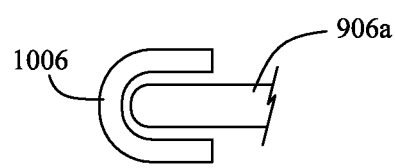

With reference to FIGS. 11A and 11B, the shaft of insertion needle 1006 may include a longitudinal opening, having a cross-sectional shape for releasably carrying the forward edge 906e of the analyte sensor (see FIG. 11B). In particular, the needle shaft 1006 may be C-, U- or V-shaped to support the sensor and limit the amount that the sensor may bend or bow during insertion. The cross-sectional width and height of insertion needle 1006 are appropriately sized to hold the sensor being inserted. In the illustrated embodiment, insertion needle 1006 is pointed and/or sharp at the tip 1012 to facilitate penetration of the skin of the patient. A sharp, thin insertion needle may reduce pain felt by the patient upon insertion of the sensor. In other embodiments, the tip of the insertion needle has other shapes, including a blunt or flat shape. These embodiments may be particularly useful when the insertion needle is not intended to penetrate the skin but rather serves as a structural support for the sensor as the sensor is pushed into the skin. As such, the sensor itself may include optional features to facilitate insertion. For example, sensor 906 may have a pointed tail portion 906b to ease insertion. In addition, the sensor may include a barb (not shown) which helps retain the sensor in the subcutaneous tissue upon insertion. The sensor may also include a notch (not shown) that can be used in cooperation with a corresponding structure (not shown) in the insertion needle to apply pressure against the sensor during insertion, but disengage as the insertion needle is removed.

Figure 10A:
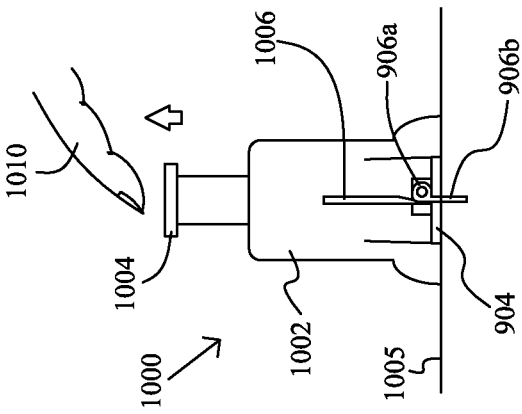
Figure 10B:
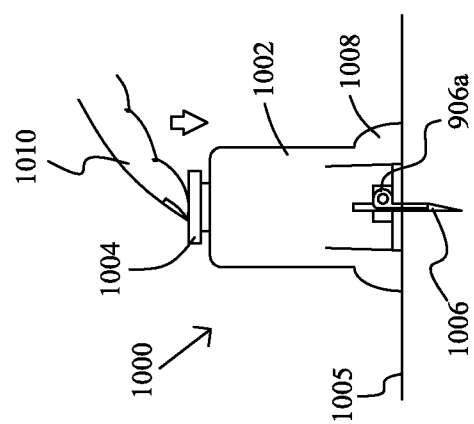
Figure 10C:
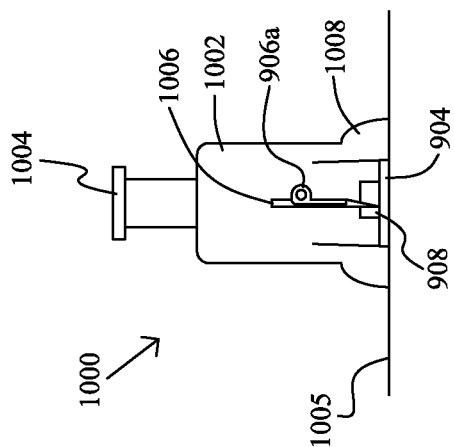

To commence the sensor insertion/transmitter mounting procedure, the front edge 906e (see FIGS. 11A and 11B) of sensor 906, which is operatively held within connector 910 (as shown in FIG. 9B but not evident in the side views provided in FIGS. 10A-10F), is slid into placed within insertion needle 1006. In turn, the pre-loaded insertion needle 1006 is operatively loaded onto the distal end of plunger 1004. Mounting base 904 with the attached connector cradle 908 is then coupled to the bottom end of insertion body 1002, such as by a snap-fit arrangement that is releasable upon complete downward displacement of plunger 1004. The collective assembly is then placed on the target skin surface 1005, as shown in FIG. 10A. The user 1010 then applies a downward force on plunger 1004, as shown in FIG. 10B, which force is transferred against insertion needle 1006 and/or sensor 906 to carry the sensor 906 into the skin 1005 of the patient. The plunger 1004 may be biased to require a certain amount of force to avoid accidental depression and to provide for very fast penetration and removal of the insertion needle from the skin. For example, a cocked or wound spring, a burst of compressed gas, an electromagnet repelled by a second magnet, or the like, may be used to provide the biasing force on plunger 1004. In one embodiment (as shown), the plunger force is applied to insertion needle 1006, and optionally to sensor 906, to push a portion of both the sensor 906 and the insertion needle 1006 through the skin 1005 of the patient and into the subcutaneous tissue. Alternatively, the force may be applied only to the sensor 906, pushing it into the skin 1005, while the insertion needle 1006 remains stationary and provides structural support to the sensor 906. In either embodiment, a hard stop to the sensor's continued penetration into the skin 1005 is provided when the connector 910 is seated within cradle 908. Once fully depressed, plunger 1004 is then released by the user 1010, as illustrated in FIG. 10C. With the upward spring biased placed on the plunger, the insertion needle is quickly retracted from the skin 1005 with sensor 906 remaining in the subcutaneous tissue due to frictional forces between the sensor and the patient's tissue. If the sensor includes the optional barb, then this structure may also facilitate the retention of the sensor within the interstitial tissue as the barb catches in the tissue. Release of plunger 1004 may also automatically decouple mounting base 904 from insertion body 1002, or a separate trigger mechanism (not shown) may be provided on the device to perform such function. The adhesive on the skin-contacting surface of base 904 retains it in place when the insertion device 1000 is removed from the skin, as illustrated in FIG. 10D. The insertion device 1000 is typically manufactured to be disposable to avoid the possibility of contamination. Alternatively, the insertion device 1000 may be sterilized and reused with only the insertion needle being disposable. After removal of the insertion device 1000 from the skin 1005, the transmitter 902 may then be manually coupled onto the mounting base 904, as shown in FIG. 10E. Specifically, the conductive pins 920 of transmitter 902 are positioned within the corresponding holes 918 within connector 910 (see FIG. 9E). In an alternate embodiment, the insertion device may be configured to mechanically mount the transmitter 902 which would be pre-mounted to the mounting base 904. In either variation, control electronics (not shown) housed within transmitter 902 enables monitoring of glucose (or other target analytes) by sensor 906 and transmission of such analyte data by transmitter 902 to the remote receiver unit (not shown) according to the pre-programmed protocols.

As mentioned previously, a battery may be provided within the transmitter housing to power the transmitter 902 as well as to provide the necessary electrical signals to sensor 906. The battery may be rechargeable/replaceable through a door (not shown) provided in the transmitter housing. To minimize the size of the on-skin unit, the battery may be relatively small, having only a moderately-lasting charge, e.g., about 3-14 days more or less. In another variation, the battery is not rechargeable or replaceable, but is disposed of along with the transmitter upon expiration of the battery charge. As this arrangement is more expensive, having a battery/transmitter that has a longer-lasting charge, e.g., about 6 months to a year may be necessary; of course, the tradeoff being a larger unit. Still yet, the transmitter may be extensively reusable with the battery being disposable along with the sensor upon expiration of the sensor's useful life, typically, between about 3 to about 14 days, in which case, the battery may be very small to last only as long as the sensor.

Figure 12A:
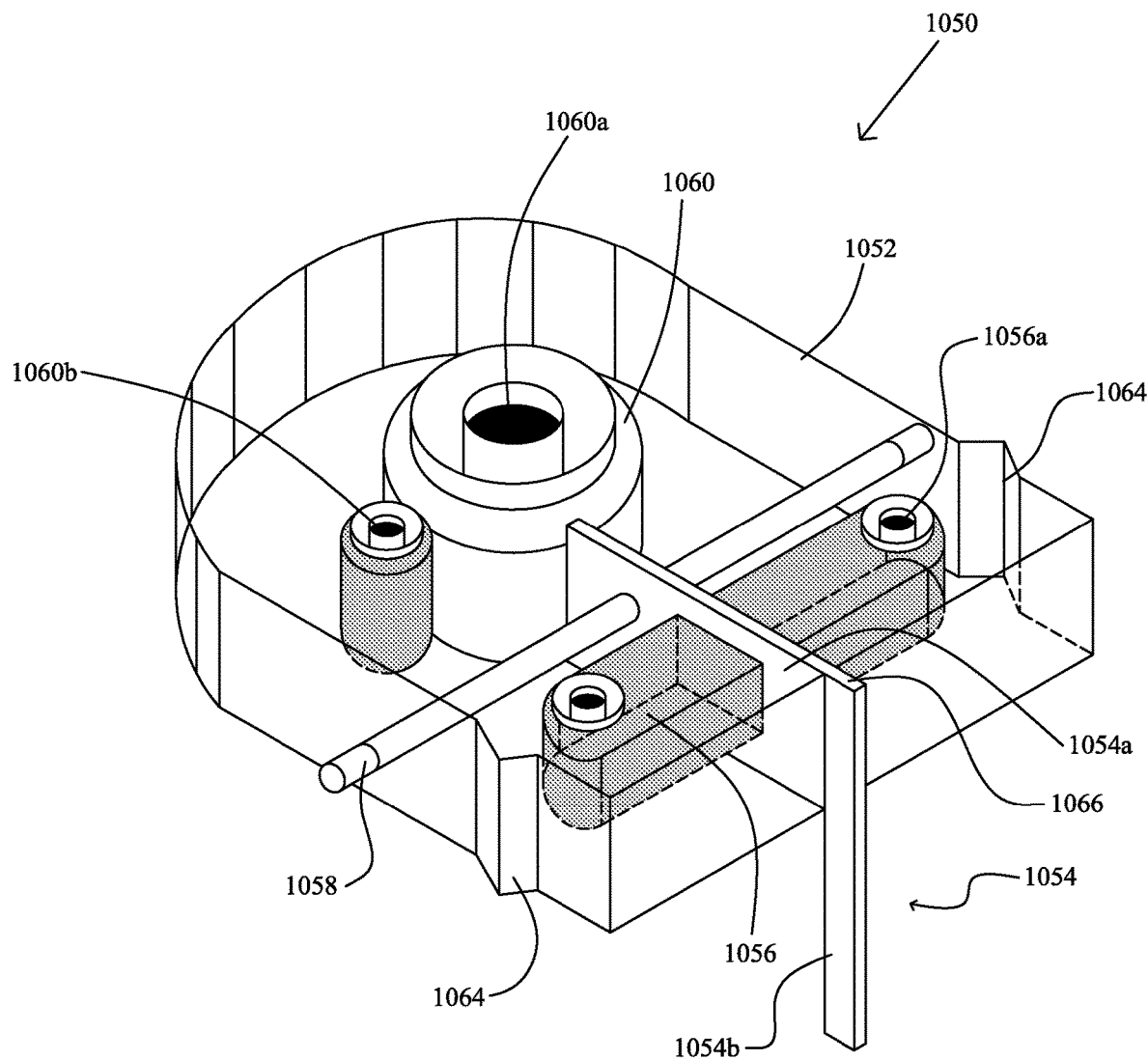
FIGS. 12A and 12B are top and bottom perspective views of another continuous analyte monitoring system of the present disclosure.
Figure 12B:
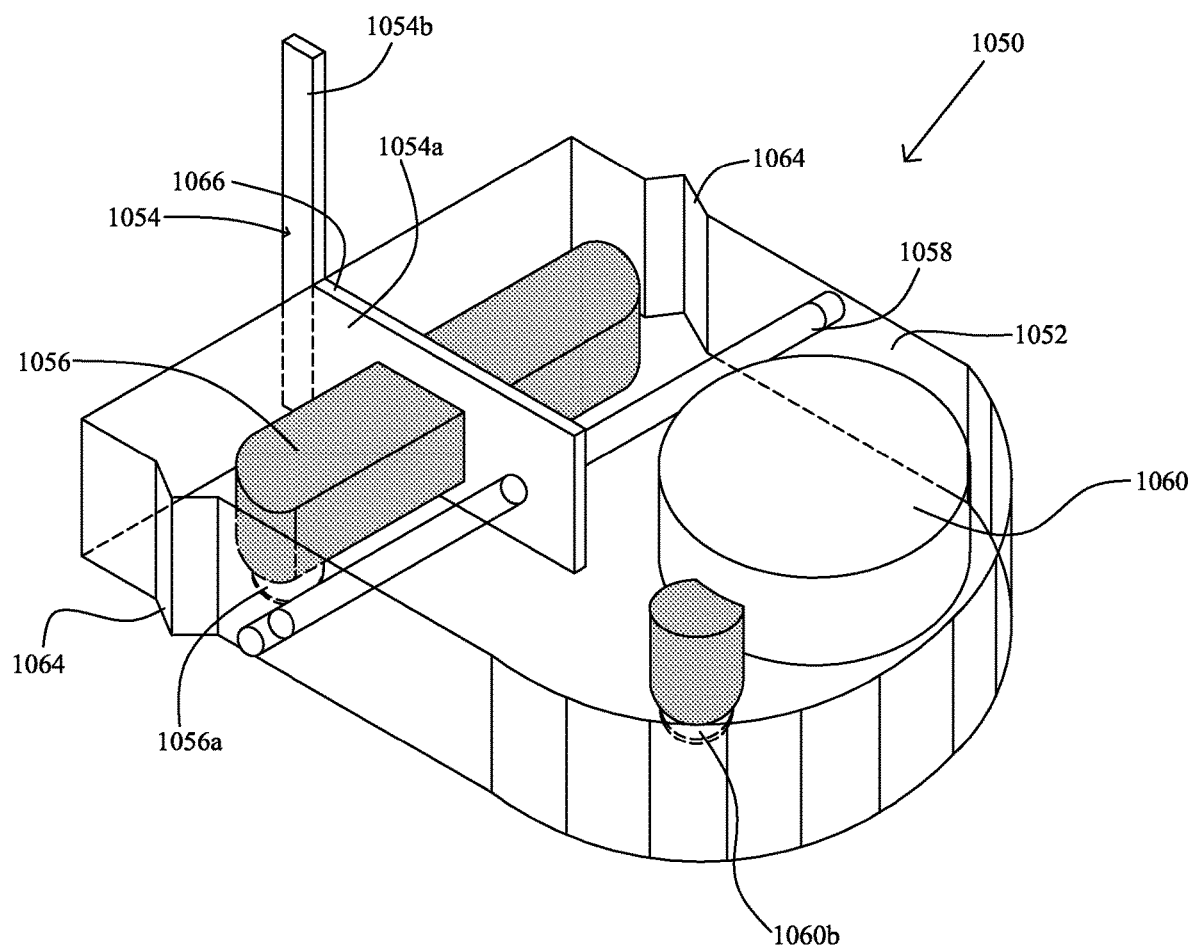

FIGS. 12A and 12B illustrate top and bottom views, respectively, of an on-skin mounting unit or base 1050 of another continuous analyte monitoring system of the present disclosure in which the battery is provided in the mounting base rather than in the transmitter. The conductive proximal portion 1054a (i.e., the electrodes) of an analyte sensor 1054 is positionable or positioned within a slot or slit 1066 within a side wall of base 1050 with the tail portion 1054b extending transversely from the base. The proximal sensor portion 1054a lies between a two-piece electrical core or connector 1056 which is permanently housed within mounting unit 1050. The connector has contacts 1056a (see FIG. 12A) which extend to a top surface 1052 of base 1050 for receiving corresponding conductive pins of the transmitter (not shown). The entire base 1050 may be fabricated of a compressible, insulating material, such as silicone. Features 1064 on opposing sidewalls of the base aligned with the ends of connector 1056 are compressible to ensure that connector 1056 maintains continuous electrical contact with sensor 1054. Such compression features 1064 may comprise a flexure such as a living hinge or the like. To prevent any movement of sensor 1054 upon placement within skin tissue, an optional alignment pin 1058 may be provided through a hole within proximal sensor portion 1054a. The opposing ends of the alignment pin 1058 may extend beyond the sidewalls of the base to physically engage with corresponding features of the transmitter (not shown) upon coupling with the base unit 1050. Also housed within base unit 1050 is a battery 1060 having high (+) and ground (−) connector contacts 1060a, 1060b, respectively. As seen in FIG. 12A, the connector contacts 1056a and battery contacts 1060a, 1060b have receptacle configurations to matingly receiving corresponding pin contacts of a transmitter (not shown) when mounted atop mounting base 1050. As such, electrical communication is established between sensor 1054 and the transmitter, and power is supplied to the transmitter and to the on-skin unit as a whole. The coupling between the transmitter and mounting base may be by way of a snap-fit arrangement between the pins and receptacles, which also allows for easy removal when replacing the base unit 1050 upon expiration of the battery 1060 and/or useful life of the sensor 1054 with the more expensive transmitter component being reusable.

All of the on-skin portions of the subject continuous monitoring systems have a very low-profile configuration. While certain embodiments have at least one dimension that is extremely small, other dimensions may be slightly greater to provide the necessary volume to house the various components of the on-skin units. For example, an on-skin unit may have a very low height dimension, but have relatively greater width and length dimensions. On the other hand, the width/length dimensions may be very small with the height being relatively greater. The optimal dimensions of a particular on-skin unit may depend on where on the body the unit is intended to be mounted. One exemplary set of dimensions for an on-skin unit of the present disclosure includes a width from about 7.5 to about 8.5 mm, a length from about 10 to about 11 mm, and a height from about 2.5 to about 3.3 mm.

Exemplary analyte monitoring systems are described in, for example, U.S. patent application Ser. No. 12/698,124 entitled "Compact On-Body Physiological Monitoring Devices and Methods Thereof" and in U.S. patent application Ser. No. 12/730,193 entitled "Methods of Treatment and Monitoring Systems for Same", the disclosures of each of which are incorporated herein by reference for all purposes. Exemplary methods and systems for inserting a an analyte sensor are described in, for example, U.S. Pat. No. 6,990,366, U.S. patent application Ser. Nos. 12/698,124, 12/698,129, now U.S. Pat. No. 9,402,544, and U.S. Provisional Application Nos. 61/238,159, 61/238,483 and 61/249,535, the disclosures of each of which are incorporated herein by reference for all purposes.

Although the subject sensors may be inserted anywhere in the body, it is often desirable that the insertion site be positioned so that the on-skin sensor control unit can be concealed. In addition, it is often desirable that the insertion site be at a place on the body with a low density of nerve endings to reduce the pain to the patient. Examples of preferred sites for insertion of the sensor and positioning of the on-skin sensor control unit include the abdomen, thigh, leg, upper arm, and shoulder.

In one embodiment, the subject sensors are injected between 2 to 12 mm into the interstitial tissue of the patient for subcutaneous implantation. Preferably, the sensor is injected 3 to 9 mm, and more preferably 5 to 7 mm, into the interstitial tissue. Other embodiments of the present disclosure may include sensors implanted in other portions of the patient, including, for example, in an artery, vein, or organ. The depth of implantation varies depending on the desired implantation target. Sensor insertion angles usually range from about 10° to about 90°, typically from about 15° to about 60°, and often from about 30° to about 45°. The construct of the insertion device, of course, will vary depending on the desired angle of insertion.

In one embodiment, a continuous analyte measurement system may include a base unit configured for mounting on a skin surface, an analyte sensor comprising two functional sides, a proximal portion configured for positioning within the base unit and a distal portion configured for insertion into the skin surface, and a conductive member positionable within the base unit and in electrical contact with the two functional sides of analyte sensor.

The proximal portion of the analyte sensor may have a planar configuration and the conductive member may be mechanically and electrically coupled to the two functional sides of the proximal portion of the analyte sensor.

The base unit may be compressible on opposing sides at least about the conductive member.

Furthermore, the system may include a component for compressing the opposing ends of the conductive member.

In one aspect, the component for compressing may be flexures on opposing sides of the base unit about the conductive member.

In another aspect, the component for compressing may be a clamping fixture positionable on opposing sides of the base unit about the conductive member.

In one aspect, the system may include an alignment pin extending through the proximal portion of the analyte sensor.

The base unit may be a non-conductive compressible material.

The non-conductive compressible material may be silicone.

The conductive connector may be a conductive compressible material.

The conductive compressible material may be carbon-doped silicone.

In a further aspect, the system may include a transmitter configured for mounting to the base unit in a low-profile manner, wherein the base unit includes a pair of receptacles for receiving a corresponding pair of conductive pins of the transmitter, and the conductive pins contact the conductive member when the transmitter is operatively mounted to the base unit.

The transmitter may mount with the base unit in a side-by-side configuration.

The transmitter may mount atop the base unit.

The transmitter may house a battery.

The base unit may house a battery.

Moreover, the base unit may include a second pair of receptacles for receiving a corresponding second pair of conductive pins of the transmitter, wherein the conductive pins contact the battery when the transmitter is operatively mounted to the base unit.

The base unit may include a cradle therein for receiving and holding the conductive member.

The cradle may compress opposing ends of the conductive member when held within the cradle.

The conductive member may include a conductive core and an insulating shell covering the conductive core.

In one aspect, the conductive member may include a non-conductive inner member within the conductive core, wherein the non-conductive inner member extends through an opening in the analyte sensor.

The base unit may include an adhesive bottom for adhering to the skin surface.

The base unit may include an opening therein through which the distal end of the analyte sensor extends.

The distal end of the analyte sensor may extend along a sidewall of the base unit.

Regarding methodology, the subject methods may include each of the mechanical and/or activities associated with use of the devices described. As such, methodology implicit to the use of the devices described forms part of the present disclosure. Other methods may focus on fabrication of such devices. The methods that may be performed according to embodiments herein and that may have been described above and/or claimed below, the operations have been described in selected typographical sequences. However, the sequences have been selected and so ordered for typographical convenience and are not intended to imply any particular order for performing the operations.

As for other details of the present disclosure, materials and alternate related configurations may be employed as within the level of those with skill in the relevant art. The same may hold true with respect to method-based aspects of the present disclosure in terms of additional acts as commonly or logically employed. In addition, though embodiments of the present disclosure have been described in reference to several examples, optionally incorporating various features, the present disclosure is not to be limited to that which is described or indicated as contemplated with respect to each variation of the present embodiments. Various changes may be made to the embodiments described and equivalents (whether recited herein or not included for the sake of some brevity) may be substituted without departing from the true spirit and scope of the present disclosure. Any number of the individual parts or subassemblies shown may be integrated in their design. Such changes or others may be undertaken or guided by the principles of design for assembly.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in the appended claims, the singular forms "a," "an," "said," and "the" include plural referents unless the specifically stated otherwise. In other words, use of the articles allow for "at least one" of the subject item in the description above as well as the claims below. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Without the use of such exclusive terminology, the term "comprising" in the claims shall allow for the inclusion of any additional element—irrespective of whether a given number of elements are enumerated in the claim, or the addition of a feature could be regarded as transforming the nature of an element set forth in the claims. Stated otherwise, unless specifically defined herein, all technical and scientific terms used herein are to be given as broad a commonly understood meaning as possible while maintaining claim validity.

In all, the breadth of the present disclosure is not to be limited by the examples provided.

What is claimed is:

1. A continuous analyte measurement system, comprising:
a memory;
a base unit configured for mounting on a skin surface;
an analyte sensor comprising a proximal portion configured for positioning within the base unit and a distal portion configured for insertion through the skin surface, wherein the analyte sensor is configured to generate one or more signals related to an analyte level; and a conductive member positionable within the base unit and in electrical contact with the analyte sensor;

wherein the continuous analyte measurement system is configured to determine the analyte level using at least a drift correction factor associated with the analyte sensor, the drift correction factor determined by an algorithm of the continuous analyte measurement system using a drift profile; and wherein the drift profile is programmed into the memory of the continuous analyte measurement system prior to insertion of the distal portion of the sensor through the skin surface.

2. The system of claim 1, wherein at least the proximal portion of the analyte sensor has a planar configuration and wherein the conductive member is mechanically and electrically coupled to the analyte sensor.

3. The system of claim 1, wherein the base unit is compressible on opposing sides at least about the conductive member, or comprises a component for compressing the opposing ends of the conductive member.

4. The system of claim 3, wherein the component for compressing comprises flexures on opposing sides of the base unit about the conductive member or else comprises a clamping fixture positionable on opposing sides of the base unit about the conductive member.

5. The system of claim 1, further comprising an alignment pin extending through the proximal portion of the analyte sensor.

6. The system of claim 1, wherein the base unit comprises a non-conductive compressible material, comprising silicone.

7. The system of claim 1, wherein the conductive member comprises a conductive compressible material, comprising carbon-doped silicone.

8. The system of claim 1, further comprising a transmitter configured for mounting to the base unit in a low-profile manner, wherein the base unit further comprises a first pair of receptacles for receiving a corresponding first pair of conductive pins of the transmitter, wherein the conductive pins contact the conductive member when the transmitter is operatively mounted to the base unit.

9. The system of claim 8, wherein the transmitter is configured to mount with the base unit in a side-by-side configuration or atop the base.

10. The system of claim 8, wherein the transmitter or the base unit houses a battery.

11. The system of claim 10, wherein the base unit houses the battery, and wherein the base unit further comprises a second pair of receptacles for receiving a corresponding second pair of conductive pins of the transmitter, wherein the conductive pins contact the battery when the transmitter is operatively mounted to the base unit.

12. The system of claim 1, wherein the base unit comprises a cradle therein for receiving and holding the conductive member, wherein the cradle compresses opposing ends of the conductive member when held within the cradle; wherein the conductive member comprises a conductive core and an insulating shell covering the conductive core; wherein the conductive member further comprises a non-conductive inner member within the conductive core; and wherein the non-conductive inner member extends through an opening in the analyte sensor.

13. The system of claim 1, wherein the base unit comprises an adhesive bottom for adhering to the skin surface or wherein the base unit comprises an opening therein through which the distal portion of the analyte sensor extends.

14. The system of claim 1, wherein the distal portion of the analyte sensor extends along a sidewall of the base unit.

15. The system of claim 1, wherein the analyte sensor does not require a user-initiated calibration during in vivo use of the analyte sensor.

16. The system of claim 1, wherein the analyte sensor comprises a plurality of electrodes including a working electrode comprising an analyte-responsive enzyme bonded to a polymer disposed on the working electrode.

17. The system of claim 16, wherein the analyte-responsive enzyme is chemically bonded to the polymer.

18. The system of claim 16, wherein the working electrode further comprises a mediator.

19. The system of claim 1, wherein the analyte sensor comprises a plurality of electrodes including a working electrode comprising a mediator bonded to a polymer disposed on the working electrode.

20. The system of claim 19, wherein the mediator is chemically bonded to the polymer.

* * * * *